United States Patent [19]
Whittaker et al.

[11] Patent Number: 5,417,712
[45] Date of Patent: May 23, 1995

[54] BONE ANCHOR

[75] Inventors: Gregory R. Whittaker, Burlington; Harold M. Martins, Newton, both of Mass.; Lehmann K. Li, Milford, Conn.

[73] Assignee: Mitek Surgical Products, Inc., Norwood, Mass.

[21] Appl. No.: 197,927

[22] Filed: Feb. 17, 1994

[51] Int. Cl.⁶ .................................... A61B 17/04
[52] U.S. Cl. ...................... 606/232; 606/72; 606/75; 606/78
[58] Field of Search ............ 606/232, 72, 75, 78

[56] References Cited

U.S. PATENT DOCUMENTS

| | | | |
|---|---|---|---|
| 4,721,103 | 1/1988 | Freedland | 606/86 |
| 4,898,156 | 2/1990 | Gatturna et al. | 606/72 |
| 4,946,468 | 8/1990 | Li | 606/232 |
| 4,968,315 | 11/1990 | Gatturna | 606/72 |
| 5,046,513 | 9/1991 | Gatturna et al. | 128/898 |
| 5,192,303 | 3/1993 | Gatturna et al. | 606/232 |
| 5,207,679 | 5/1993 | Li | 606/232 |
| 5,217,486 | 6/1993 | Rice et al. | 606/232 |
| 5,306,290 | 5/1994 | Martins et al. | 606/232 |

*Primary Examiner*—Stephen C. Pellegrino
*Assistant Examiner*—Gary Jackson
*Attorney, Agent, or Firm*—Pandiscio & Pandiscio

[57] ABSTRACT

An improved anchoring device for use in bone holes, bone tunnels and other assorted workpieces, and being particularly compatible with fabrication from both polymeric and bioabsorbable materials. The improved anchoring device has novel fastening means which permit the anchor to be fastened within a bone hole or bone tunnel while minimizing the stress induced on the body of the anchor during installation.

34 Claims, 18 Drawing Sheets

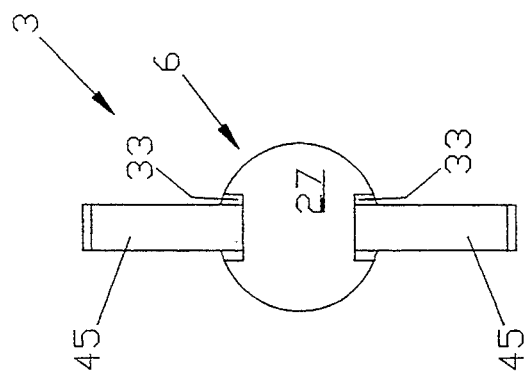
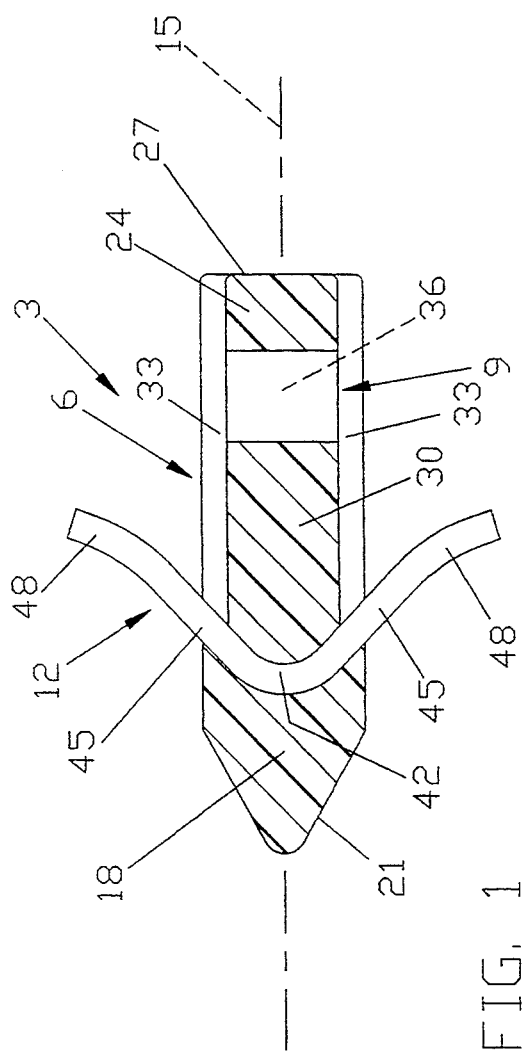
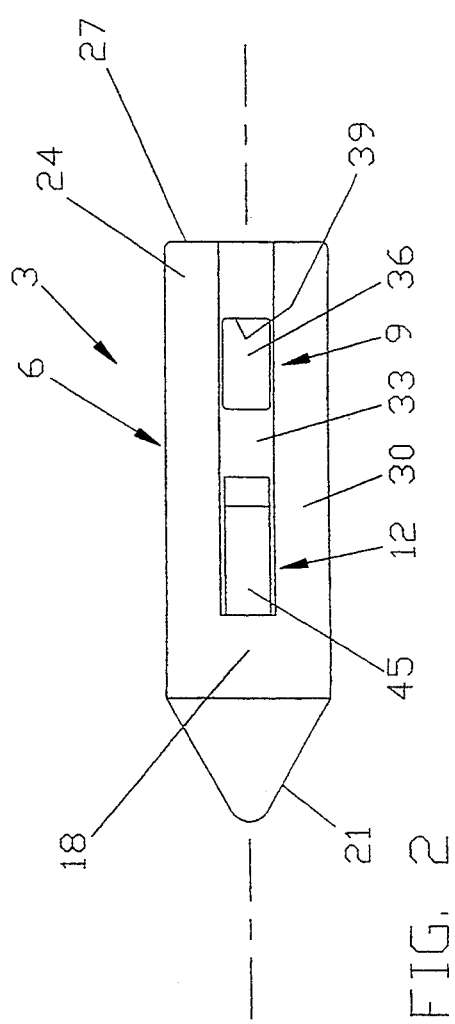

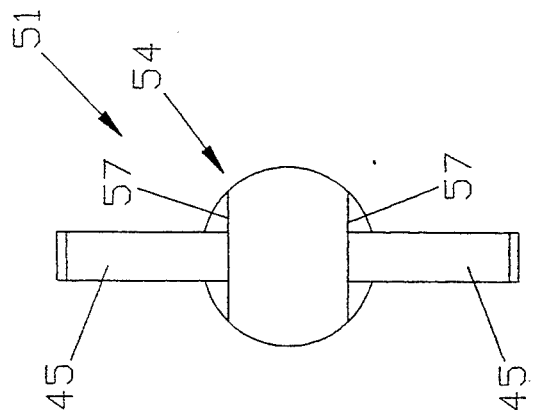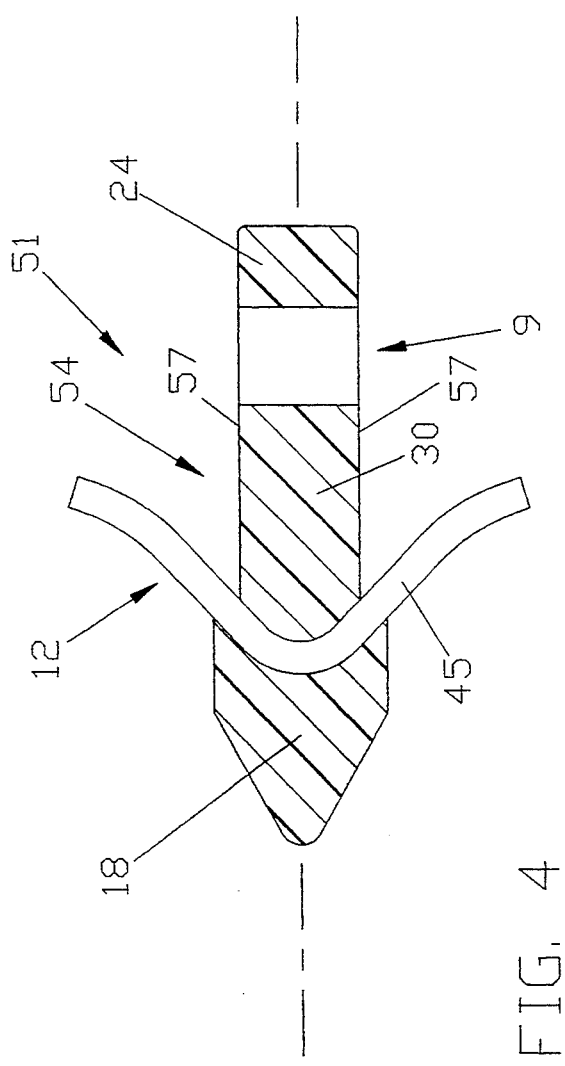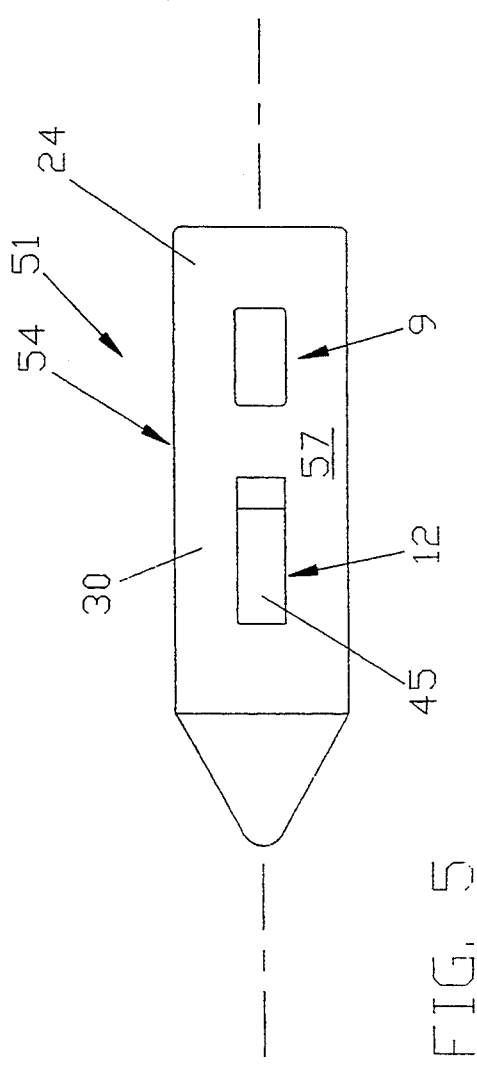

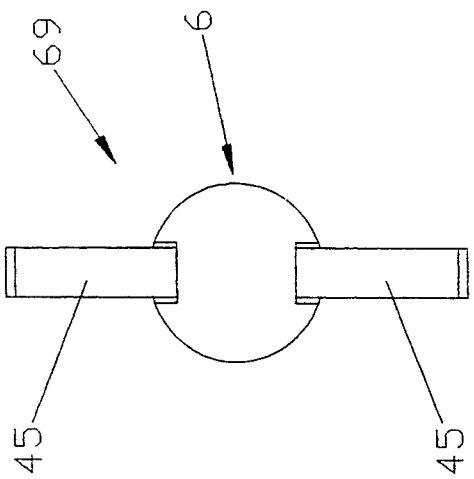
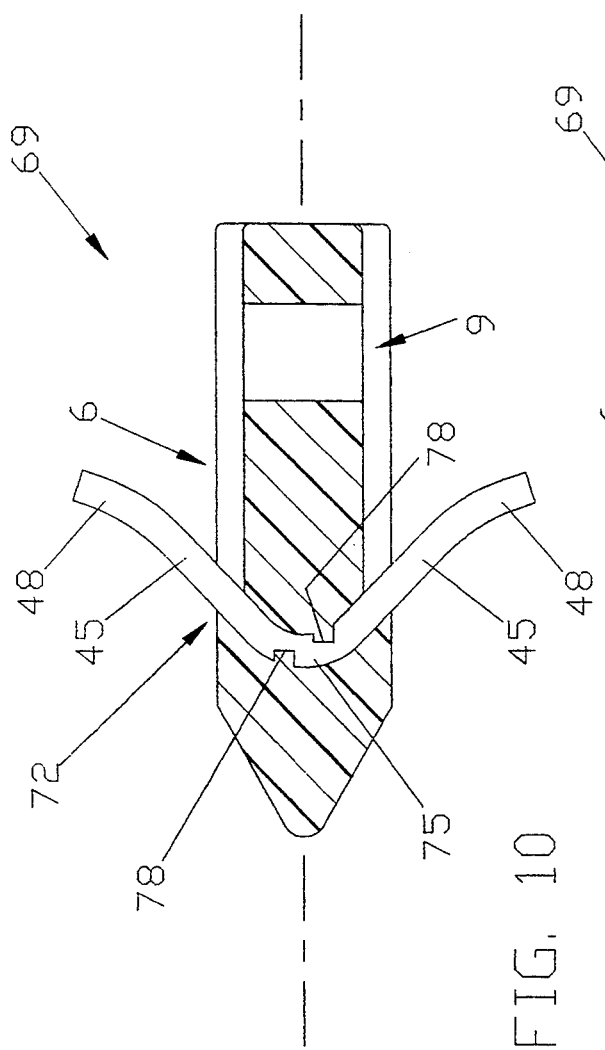
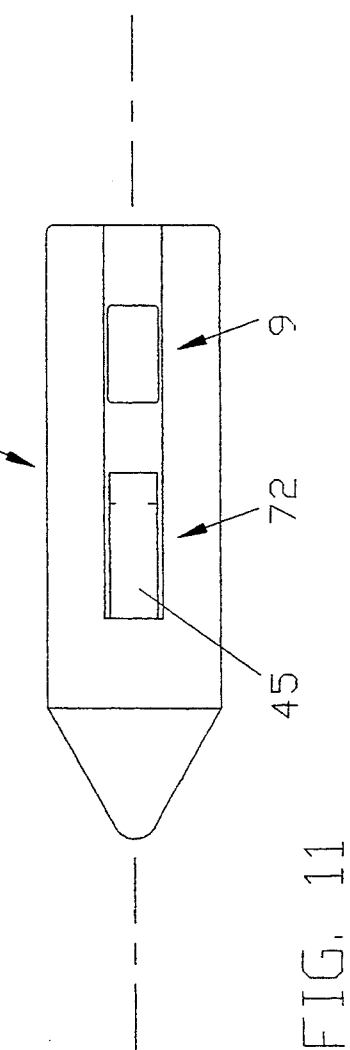

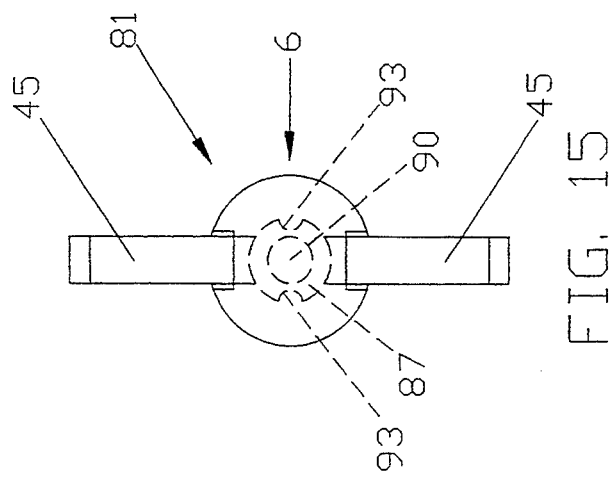
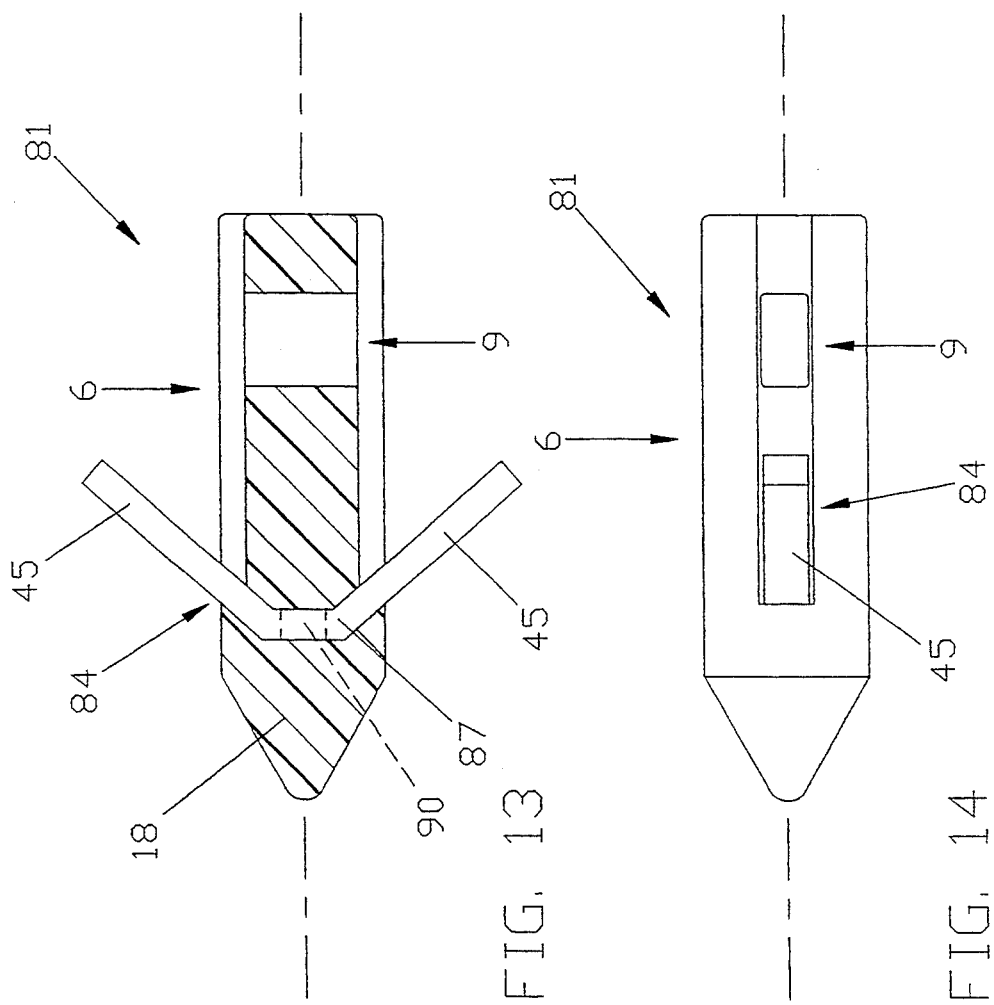

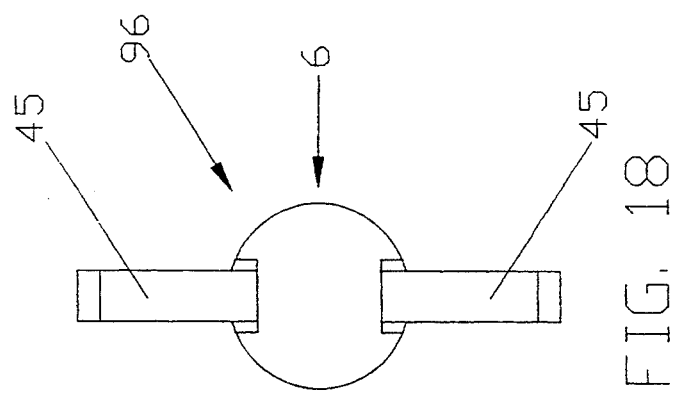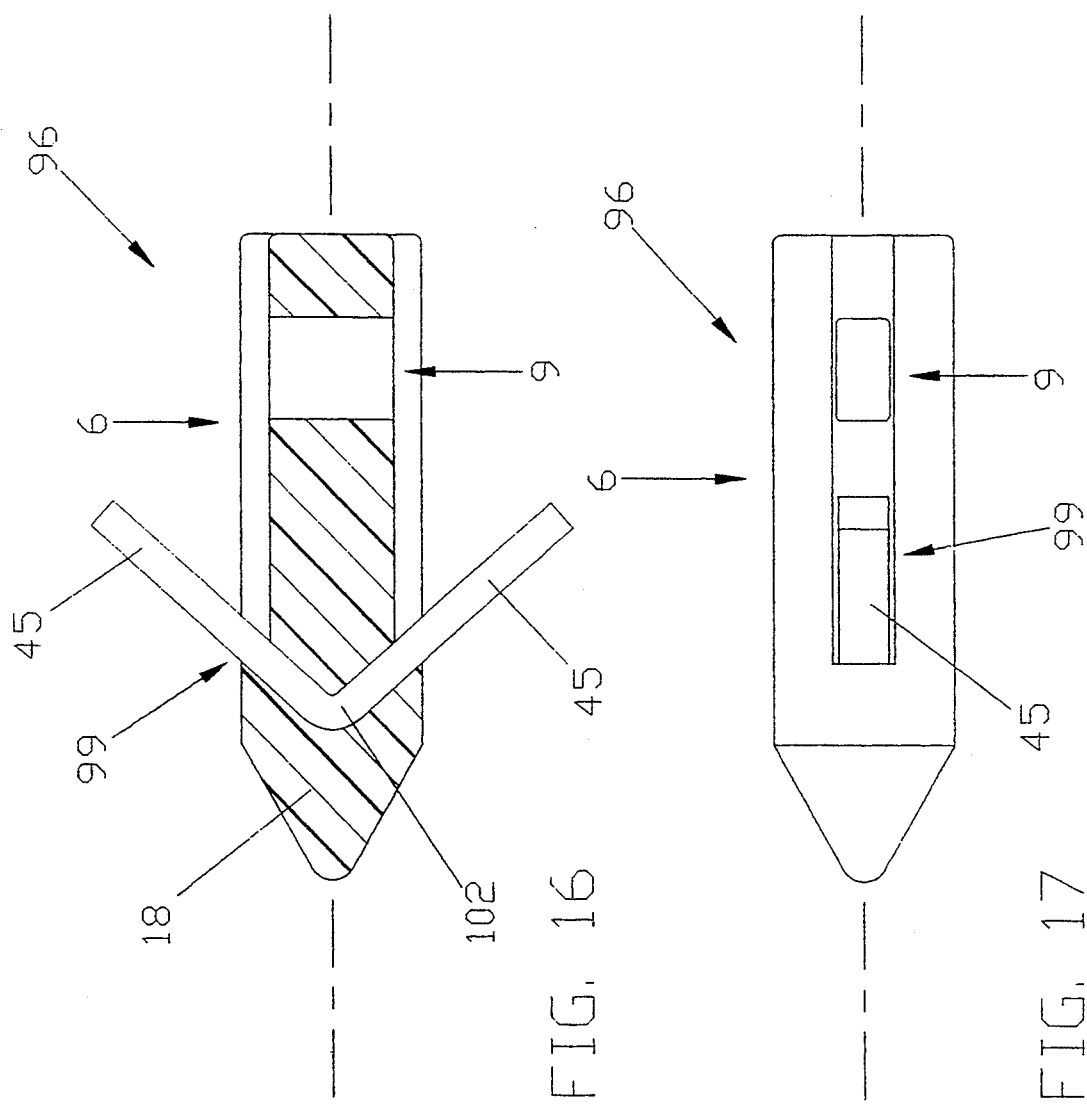

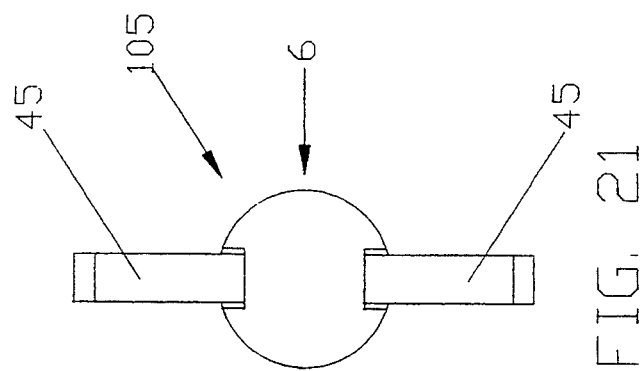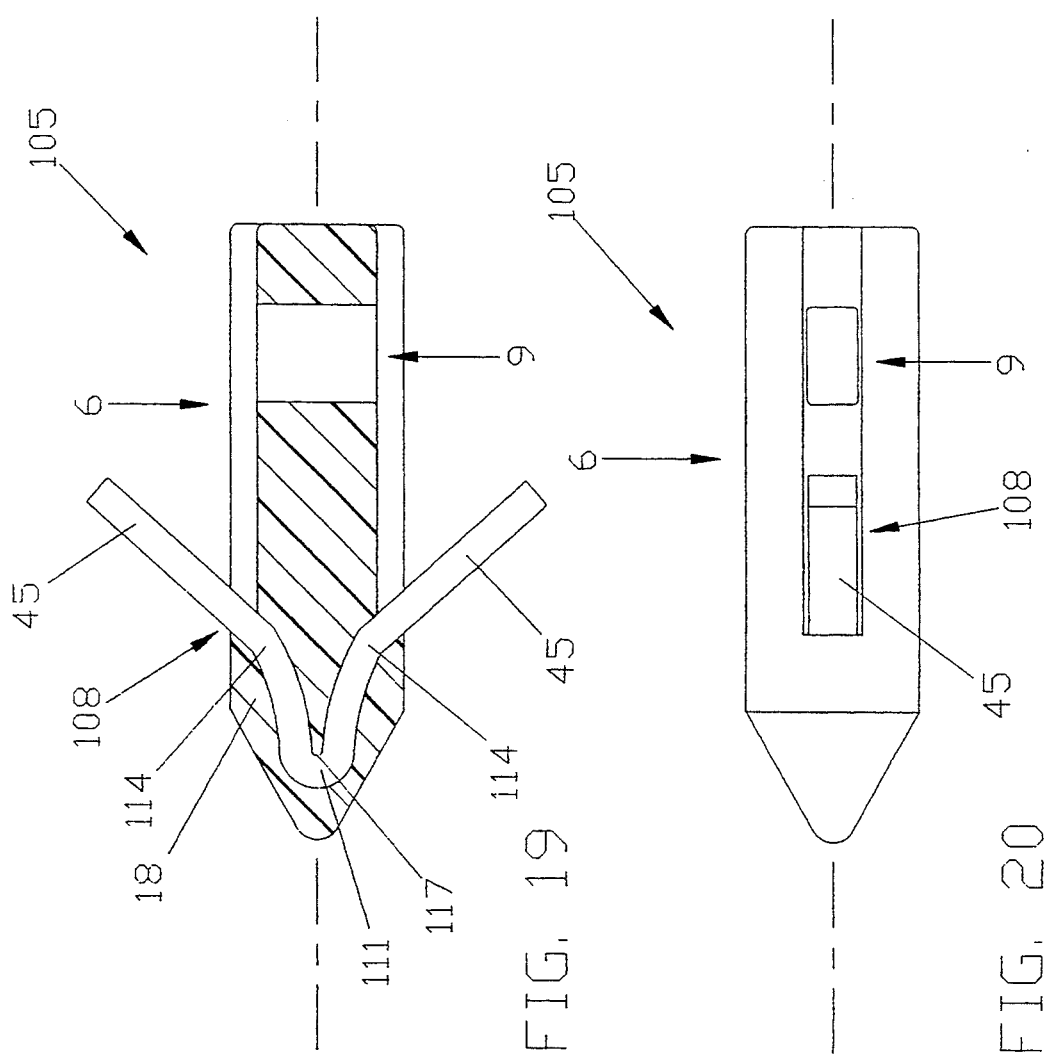

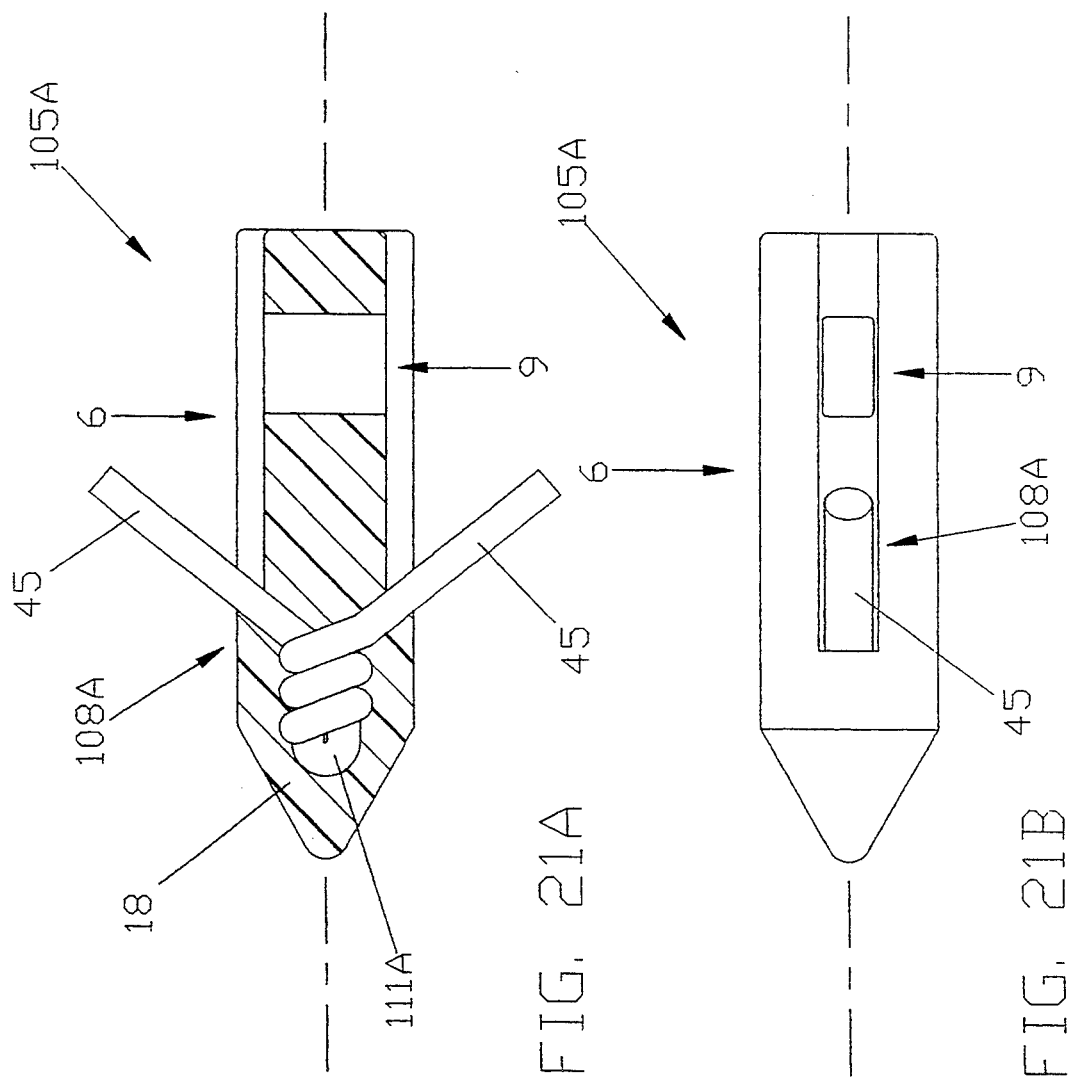

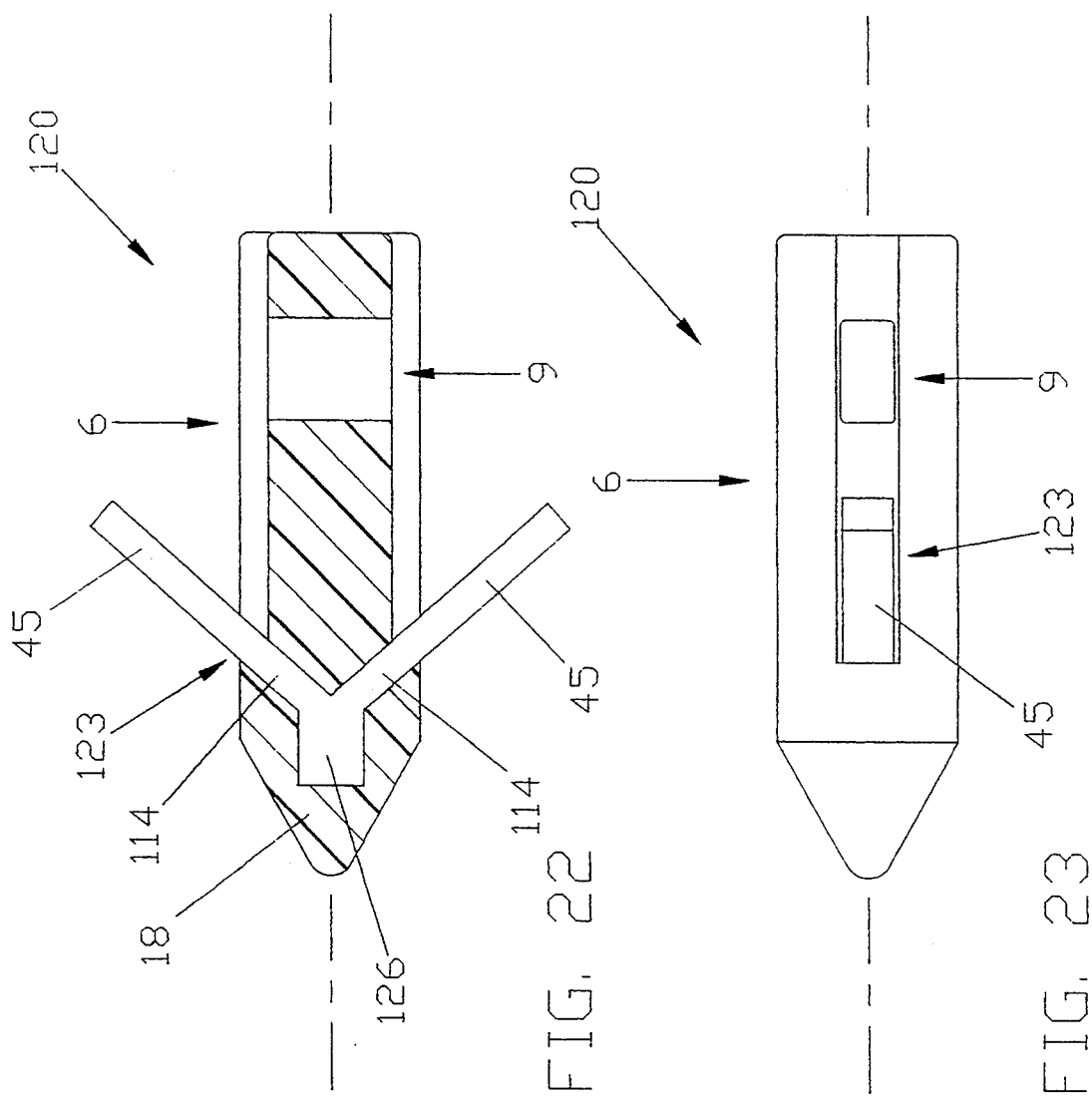

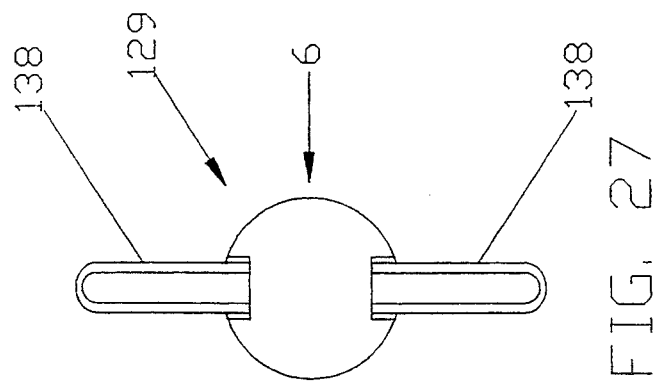
FIG. 27
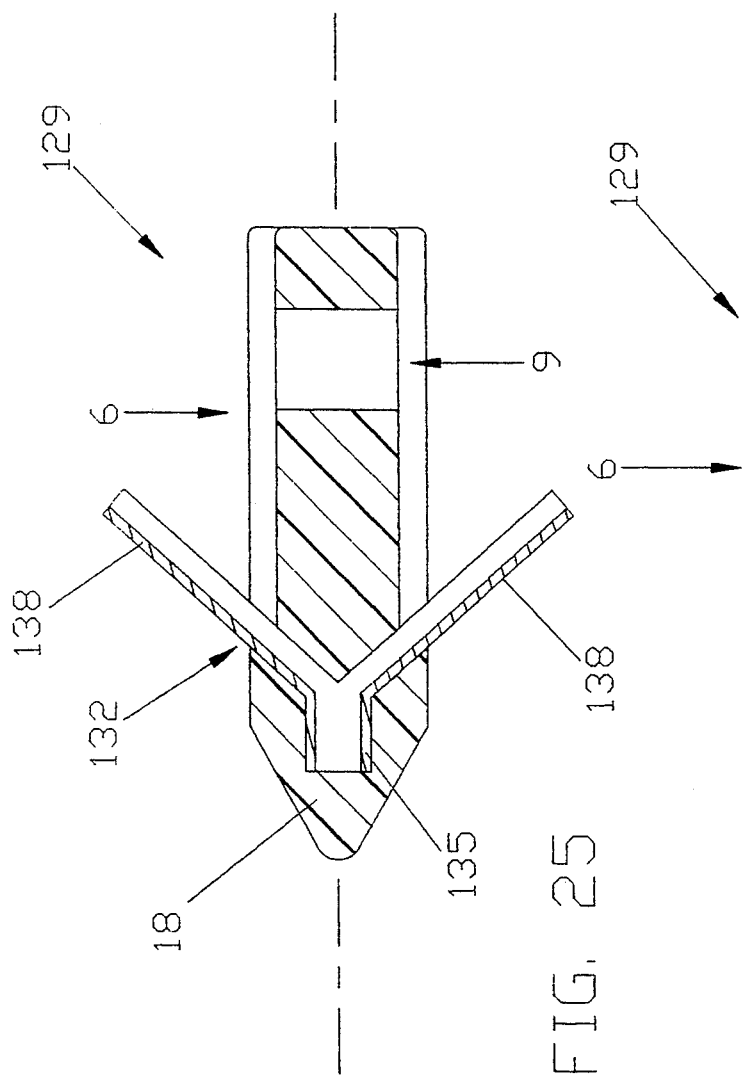
FIG. 25
FIG. 26

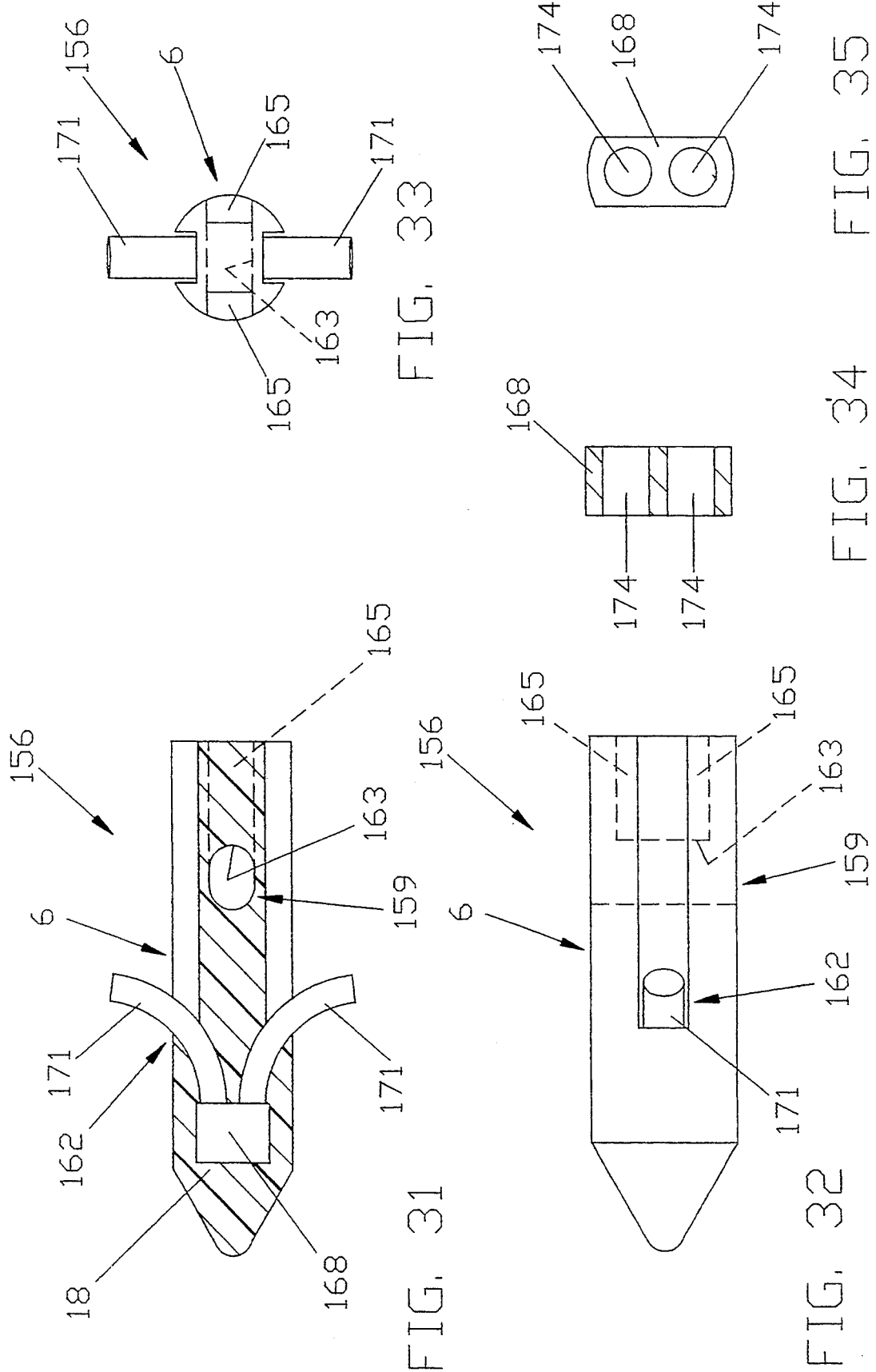

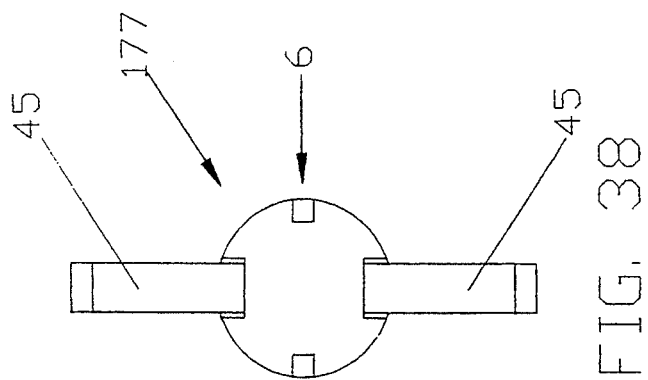
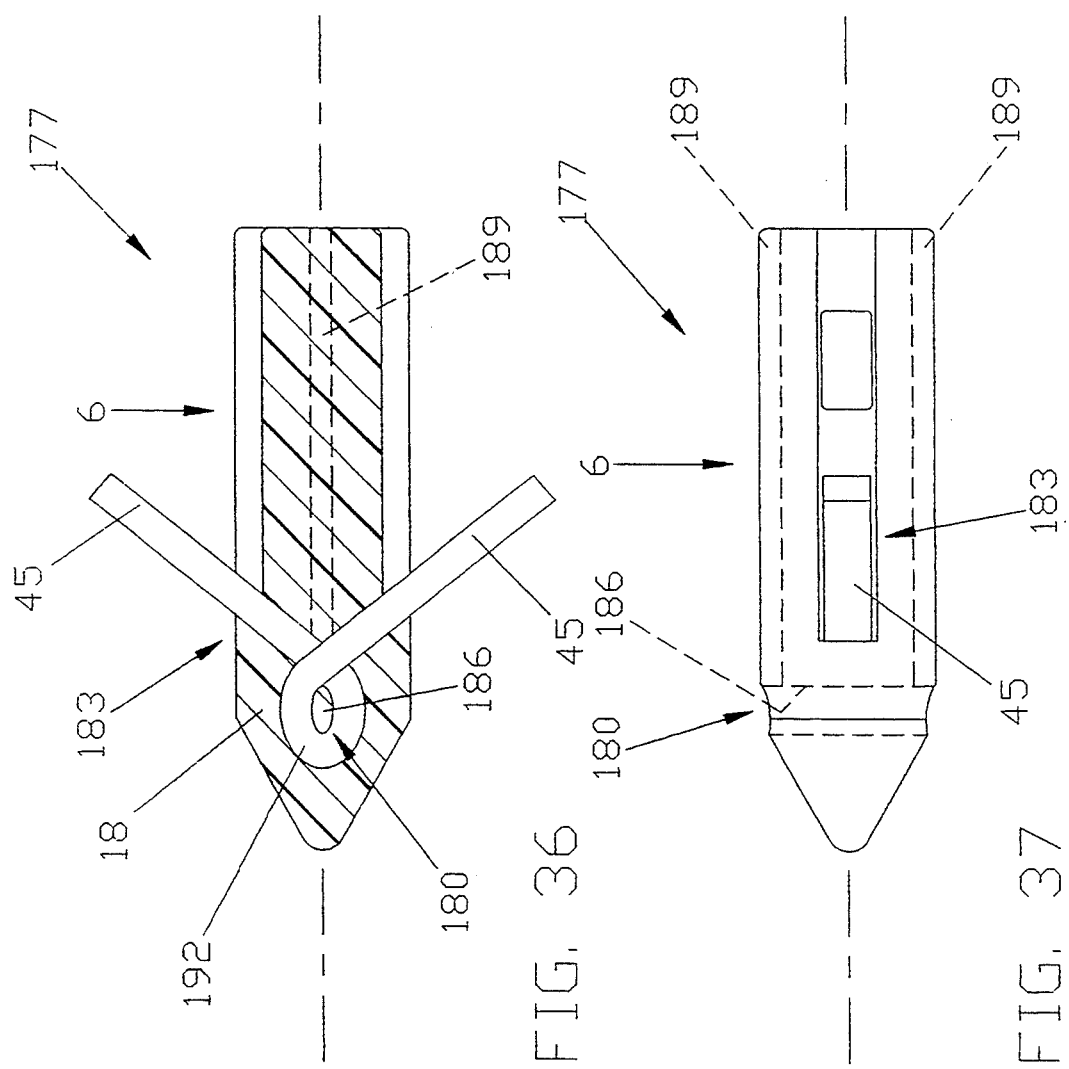

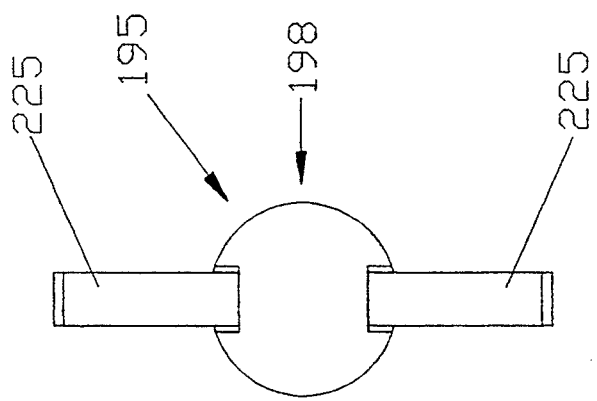
FIG. 41
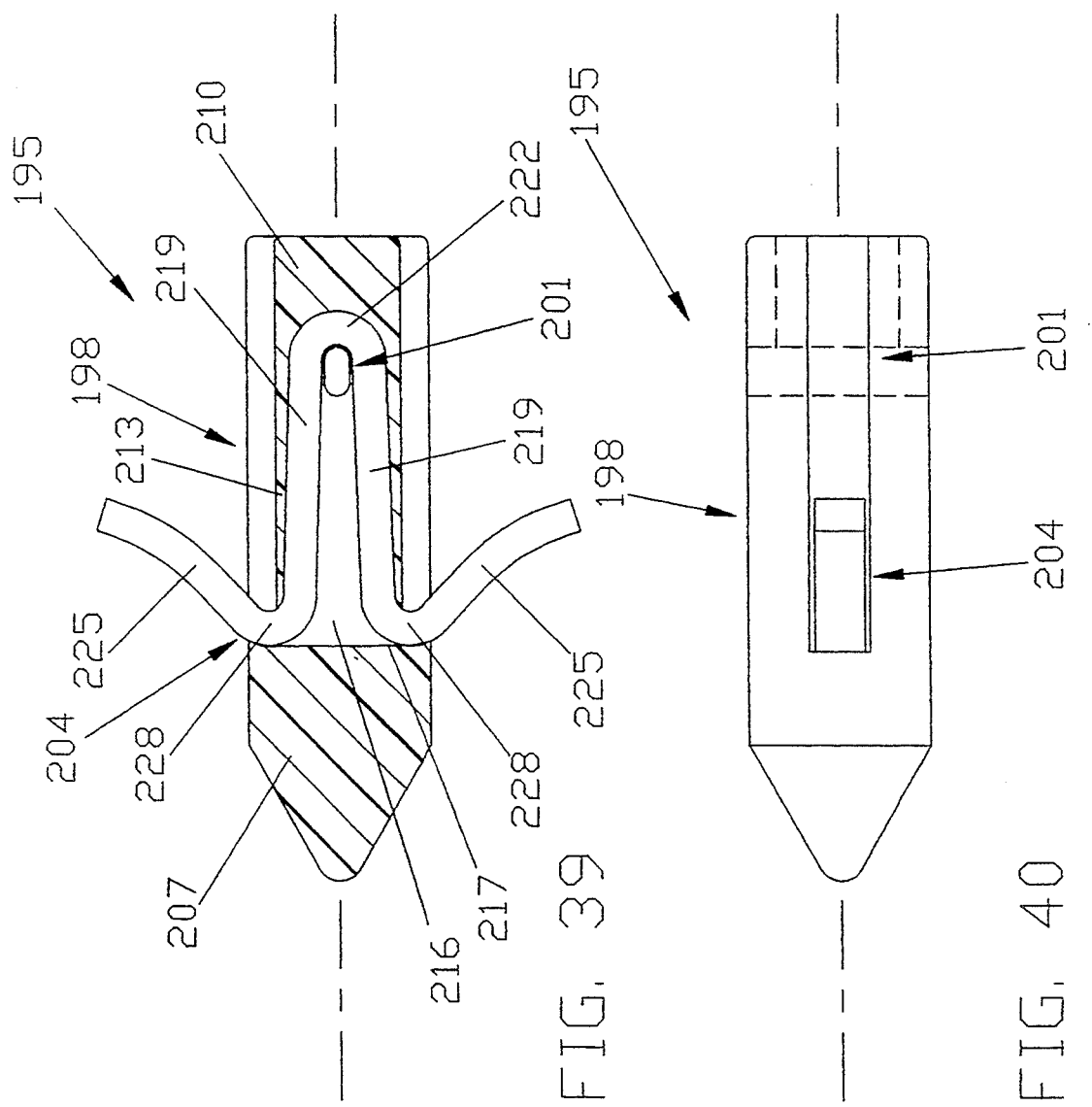
FIG. 39
FIG. 40

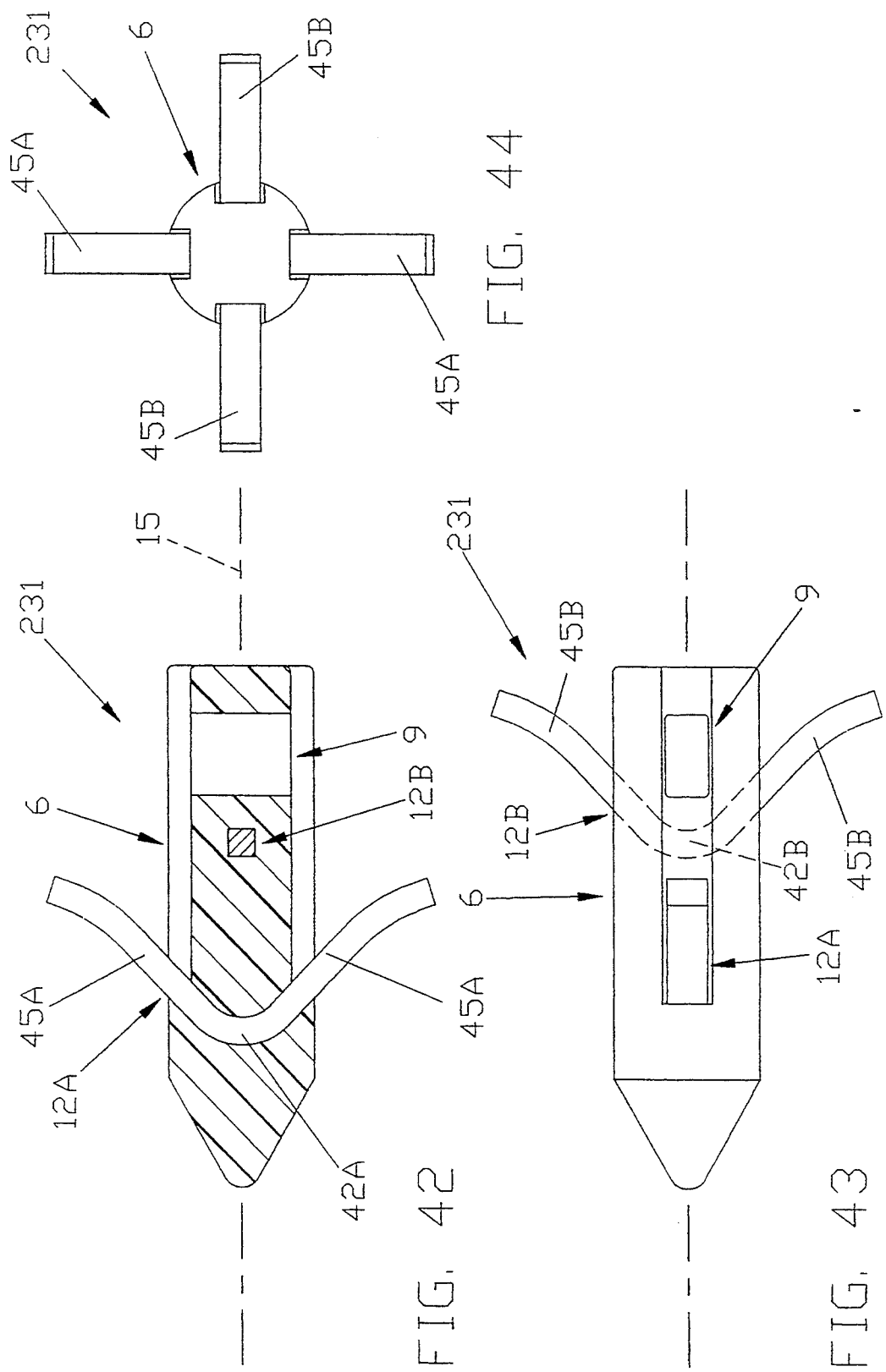

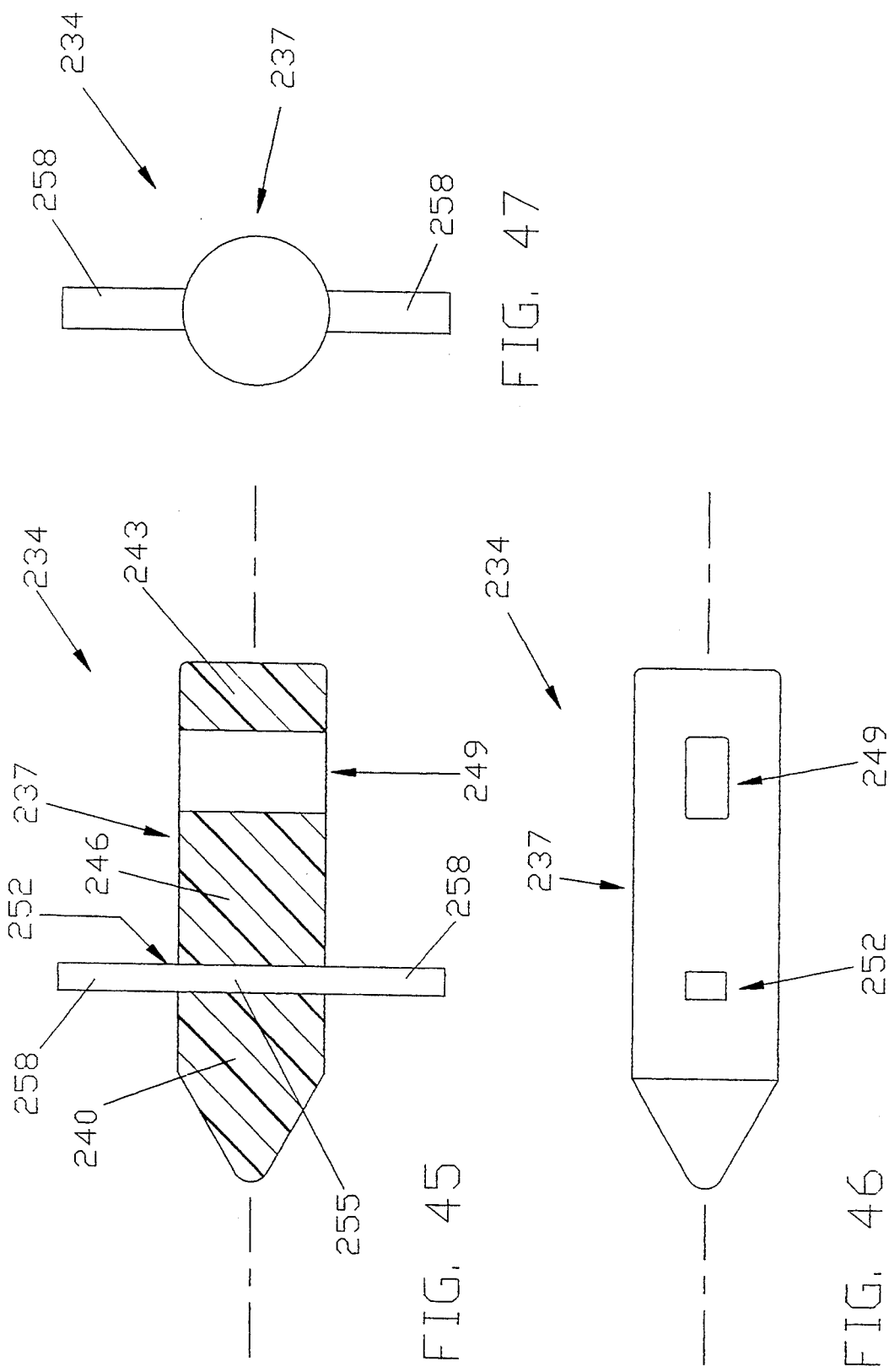

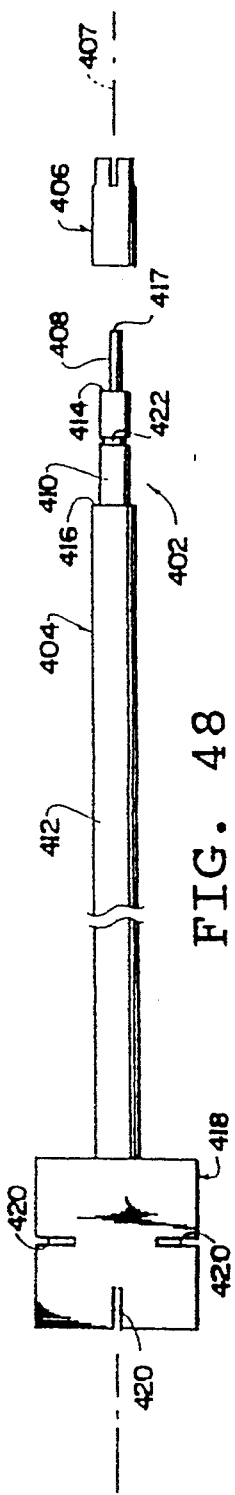
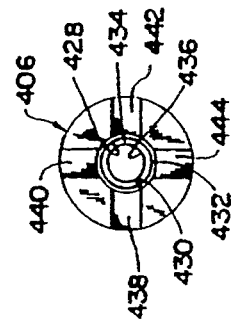
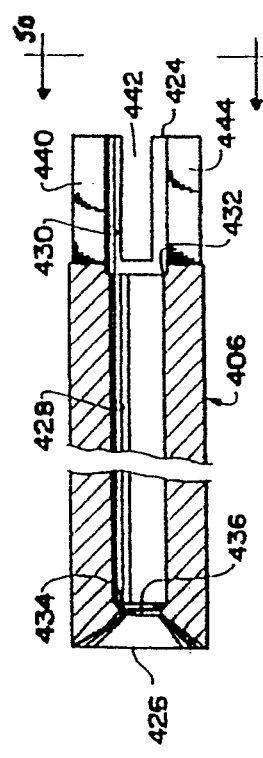
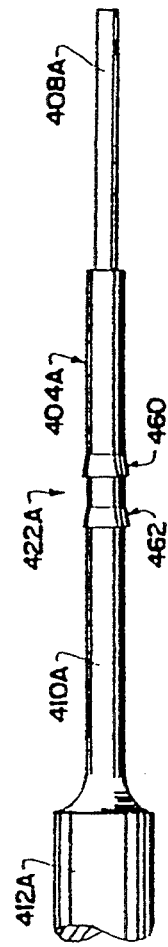
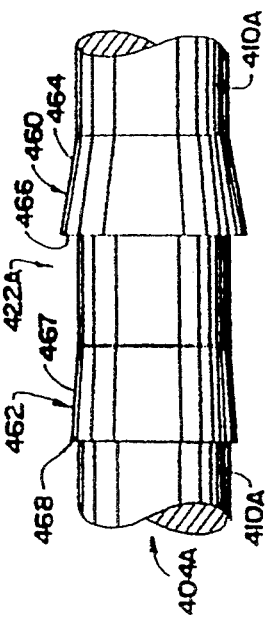

BONE ANCHOR

FIELD OF THE INVENTION

The present invention relates generally to fastening devices. More particularly, the present invention relates to anchoring devices for fixedly attaching an object to a workpiece, and installation tools for deploying such anchoring devices. Still more particularly, the present invention relates to bone anchors for anchoring an object to bone.

BACKGROUND OF THE INVENTION

In U.S. Pat. Nos. 4,632,101; 4,721,103; 4,898,156; 4,968,315; 4,997,433; 5,037,422; 5,147,362; 5,207,679; and 5,217,486, there are disclosed a variety of anchors for attaching suture, bone and/or soft tissue to bone. The foregoing patents further disclose a number of installation tools for deploying the anchors disclosed therein. Complete details of the construction and operation of these anchors and their associated installation tools are provided in the above-identified patents, which patents are hereby incorporated herein by reference.

It will, therefore, be understood that anchoring devices such as those taught in the above-referenced patents generally comprise an anchor body, attachment means for attaching the desired object to the anchor body, and one or more barbs, pins, ridges, threads, or other bone-engaging means for holding the anchor body securely to the bone. Typically, the bone-engaging means are either manufactured separately from the body and then assembled to it, or they are machined/milled from the body itself.

Prior art bone-engaging means often take the form of several straight or curved cantilevered barbs, where the barbs may be elastically deformed to permit installation. This has been particularly true for anchors used in medical applications, where the need for high holding strengths has lead to the development of anchors having multiple cantilevered barbs. In any case, the body, the attachment means, and the bone-engaging means mechanically cooperate with one another to fasten a suture, bone portion, soft tissue, prosthesis, post or other object in a bone hole or bone tunnel.

Those skilled in the art will appreciate that known bone anchors generally experience a wide range of stresses during insertion into a bone hole or bone tunnel. Although some prior art anchors have attempted to incorporate polymeric materials in their construction, these anchors have, in practice, generally provided inadequate holding strength. As a consequence, known anchor bodies and known bone-engaging means have generally been made from high strength, biocompatible metals and metal alloys.

As the use of prior art anchoring devices has become more widespread, however, it has been found that known bone anchors suffer from a number of limitations. For example, forming both the anchor body and the bone-engaging means out of biocompatible metals and metal alloys increases the cost of manufacturing. Also, in many medical applications, it may be desirable to minimize the metal remaining in the patient's body after surgery.

Until now, however, the mechanical requirements placed on known anchors have generally limited the extent to which it was possible to incorporate alternate materials into the anchors.

For example, a large number of different biocompatible polymeric and bioabsorbable materials are currently available which are: (i) relatively low in cost; (ii) fully compatible with conventional fabrication methods; and (iii) capable of being absorbed into the body of the patient after surgery. Unfortunately, such polymeric and bioabsorbable materials generally do not possess the requisite mechanical properties that have been found to be necessary for adequate retention of the anchor in the bone hole or bone tunnel. In particular, it has been found that with "barb-type" prior art anchor designs, the anchor bodies cannot be formed out of these alternative materials since the materials have insufficient structural strength to hold the inboard ends of the prior art barbs fast. At the same time, the anchor barbs themselves cannot be formed out of these alternative materials since the materials have insufficient elasticity to permit anchor deployment and insufficient strength to hold the anchor fast to the bone.

With regard to the anchor bodies, it should be appreciated that substantial stresses may be induced in the prior art anchor bodies during both construction and use. For example, during the construction of some anchors, the inboard end of a curved barb is forced into a straight channel in the anchor body. This tends to induce significant stresses in the anchor body. Furthermore, in some anchors, significant stresses are induced in the anchor bodies during use when the barbs are deformed through engagement with a bone. Unfortunately, the aforementioned polymeric and bioabsorbable materials lack the structural strength of the aforementioned biocompatible metals, and hence anchors formed out of such polymeric and bioabsorbable materials using prior art designs tend to lack the requisite holding power.

It has been, therefore, impractical to incorporate the aforementioned polymeric and bioabsorbable materials into known anchor body designs.

OBJECTS AND SUMMARY OF THE INVENTION

Accordingly, a primary object of the present invention is to provide an improved anchoring device which is adapted to be constructed from a variety of different materials.

A more specific object of the present invention is to provide an improved anchoring device which may be made out of both polymeric and bioabsorbable materials.

Another object of the present invention is to provide an improved anchoring device having fastening means for fastening the anchor within a bone hole or bone tunnel, wherein the fastening means comprise multiple bone-engaging means.

Yet another object of the present invention is to provide a novel anchor having an improved design adapted to reduce the stresses induced in the anchor's body when the anchor's barbs are deformed during use.

A still further object of the present invention is to provide a novel anchor whose holding strength is equal to or better than the holding strength of prior art anchors.

Yet another object of the present invention is to provide an anchor wherein substantially no stresses are induced in the anchor body while assembling the anchor's bone-engaging means to the body.

Another object of the present invention is to provide a bone anchor which may be manufactured using both conventional polymer molding technology and metal-forming technology.

Still another object of the present invention is to provide a novel anchor which may be deployed using existing anchor installation tools.

A further object of the present invention is to provide a novel bone anchor having a reduced manufacturing cost.

Still another object of the present invention is to provide an improved anchor for attaching a suture, bone, soft tissue, prosthesis, post or other object to bone.

And another object is to provide an improved method for attaching an object to bone.

These and other objects of the present invention are achieved through the provision and use of a novel anchor design which comprises a body, attachment means for attaching the desired object to the body, and fastening means for fastening the anchor within a bone hole or bone tunnel.

The anchor body comprises a distal portion having a first end and a second end, a proximal portion having a first end and a second end, and a middle portion extending from the second end of the distal portion to the first end of the proximal portion. In the preferred embodiment of the invention, the anchor body preferably comprises a polymeric or bioabsorbable material.

Attachment means for attaching the desired object to the anchor are formed in a portion of the body. In a preferred embodiment, the attachment means comprise a round or elongated hole extending diametrically through a portion of the anchor body.

The fastening means comprise a central portion and a plurality of bone-engaging means. The central portion is fixedly positioned within the novel anchor body and is formed out of a resilient material. Each of the plurality of bone-engaging means is connected to the central portion and extends outwardly from the anchor body. In a preferred embodiment, the bone-engaging means are also formed out of an elastically deformable material.

The foregoing anchor is intended to be used in conjunction with an appropriate installation tool of the sort well known in the art. In a preferred embodiment, the installation tool comprises an elongated shaft having a distal end and a proximal end. Tubular means, associated with the distal end of the shaft, are adapted to receive and hold the middle and proximal portions of the novel anchor's body. During use, the distal end of the shaft moves axially through the tubular means so as to engage the anchor and drive it out of the tubular means and into an adjacent bone hole or bone tunnel.

BRIEF DESCRIPTION OF THE DRAWINGS

These and other objects, features and advantages of the present invention will be more fully disclosed in, or rendered obvious by, the following detailed description of the preferred embodiments of the invention, which are to be considered together with the accompanying drawings wherein like numbers refer to like parts and further wherein:

FIG. 1 is a top view, partially in section, of a preferred embodiment of the present invention;

FIG. 2 is a side elevational view of the anchor shown in FIG. 1;

FIG. 3 is a rear end view of the anchor shown in FIG. 1;

FIG. 4 is a top view, partially in section, of an alternative embodiment of the present invention, showing a variation of the anchor body shown in FIGS. 1-3;

FIG. 5 is a side elevational view of the anchor shown in FIG. 4;

FIG. 6 is a rear end view of the anchor shown in FIG. 4;

FIG. 10 is top view, partially in section, of an alternative embodiment of the present invention, showing a variation of the fastening means shown in FIGS. 1-3, wherein the central portion of the fastening means is notched;

FIG. 11 is a side elevational view of the anchor shown in FIG. 10;

FIG. 12 is a rear end view of the anchor shown in FIG. 10;

FIG. 13 is a top view, partially in section, of a further alternative embodiment of the present invention, showing another variation of the fastening means shown in FIGS. 1-3, wherein the central portion of the fastening means is flattened and includes a hole therethrough;

FIG. 14 is a side elevational view of the anchor shown in FIG. 13;

FIG. 15 is a rear end view of the anchor shown in FIG. 13 and further illustrating, in phantom, the flattened central portion having a hole therethrough, and including indented portions circumferentially positioned around the peripheral edge of the flattened central portion;

FIG. 16 is a top view, partially in section, of a further alternative embodiment of the present invention, showing another variation of the fastening means shown in FIGS. 1-3;

Figure 30:
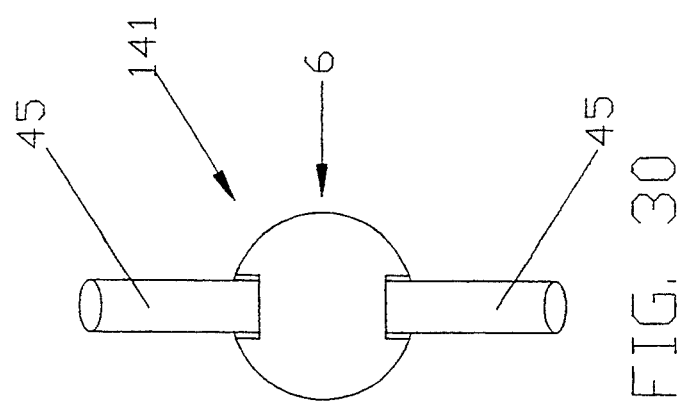
Figure 28:
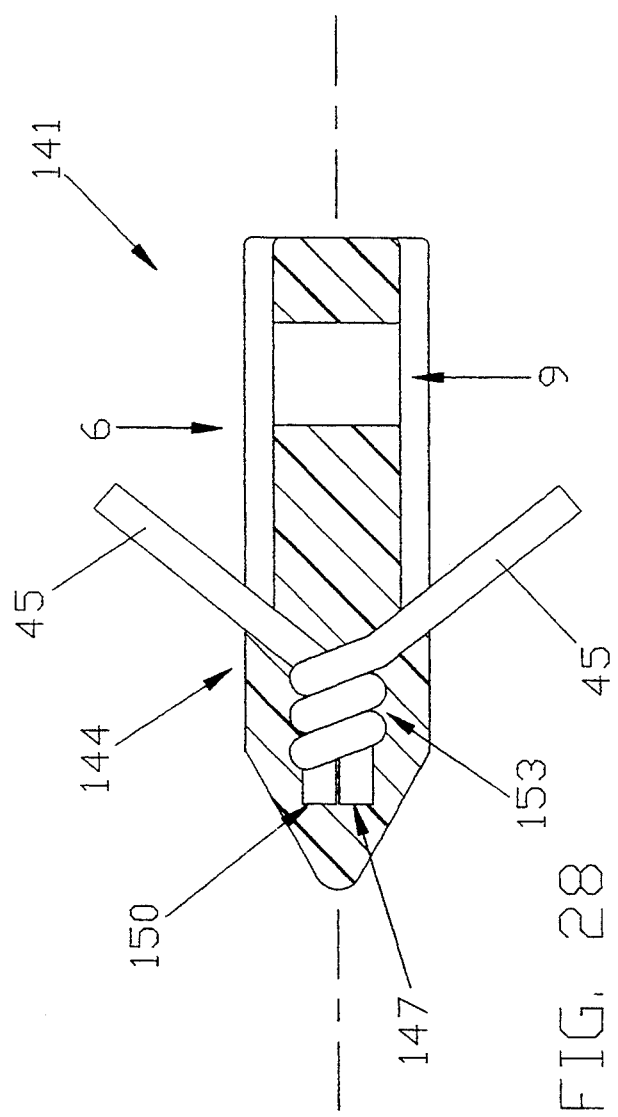
Figure 29:
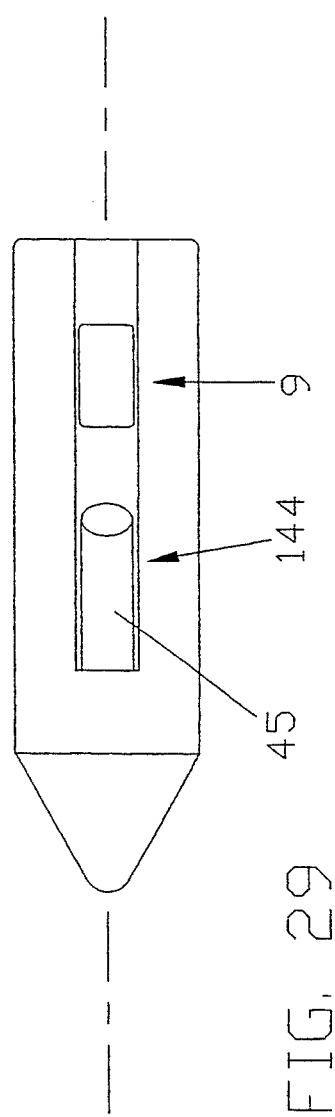
Figure 51:
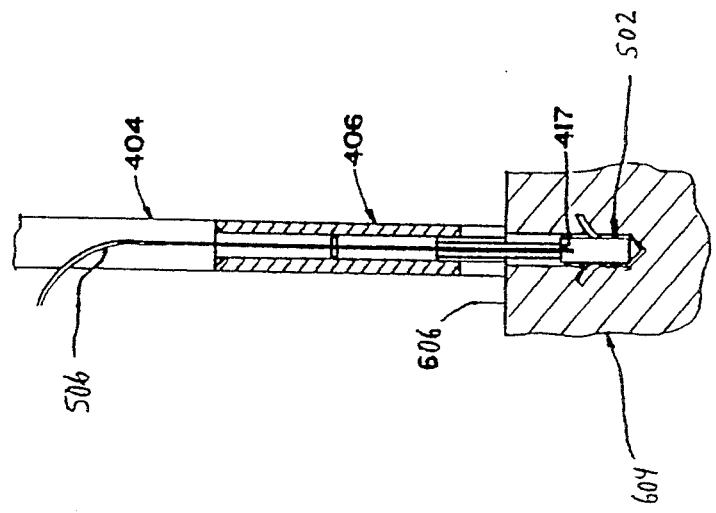
Figure 52:
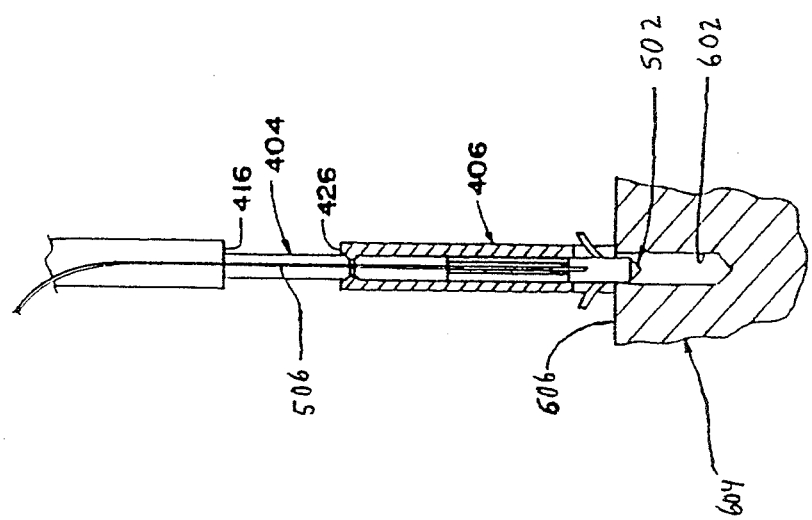
Figure 53:
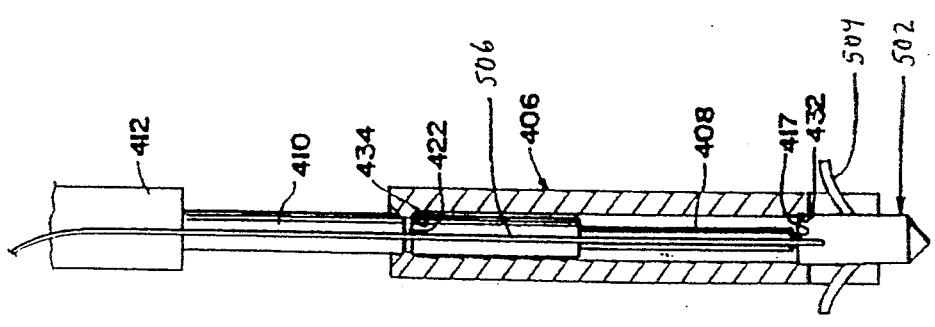

Fig.,17 is a side elevational view of the anchor shown in FIG. 16;

FIG. 18 is a rear end view of the anchor shown in FIG. 16;

FIG. 19 is a top view, partially in section, illustrating a further alternative embodiment of the present invention, showing another variation of the fastening means shown in FIGS. 1-3, wherein the fastening means has a linear projection formed in the central portion thereof;

FIG. 20 is a side elevational view of the anchor shown in FIG. 19;

FIG. 21 is a rear end view of the anchor shown in FIG. 19;

FIG. 21A is a top view, partially in section, of a further alternative embodiment of the present invention, showing a variation of the fastening means shown in FIG. 19, wherein the fastening means has a twisted linear projection formed in the central portion thereof;

FIG. 21B is a side elevational view of the anchor shown in FIG. 21A;

FIG. 21C is a rear end view of the anchor shown in FIG. 21A;

FIG. 22 is a top view, partially in section, illustrating a further alternative embodiment of the present invention, showing still another variation of the fastening means shown in FIGS. 1–3, wherein the fastening means comprise a bar which has been split through a portion of its length so as to provide the desired bone-engaging means, and further wherein the fastening means comprise a linear projection at the central portion thereof which extends into the distal portion of the anchor body;

FIG. 23 is a side elevational view of the suture anchor shown in FIG. 22;

FIG. 24 is a rear end view of the anchor shown in FIG. 22;

FIG. 25 is a top view, in section, illustrating a further alternative embodiment of the present invention, showing yet another variation of the fastening means shown in FIGS. 1–3, wherein the fastening means are formed from a tube which has been split part way along its length, and further wherein a distal portion of the tube is filled with polymer;

FIG. 26 is a side elevational view of the anchor shown in FIG. 25, and further illustrating the arcuate cross-section of the bone-engaging means;

FIG. 27 is a rear end view of the anchor shown in FIG. 25 and also illustrating the arcuate cross-section of the bone-engaging means;

FIG. 28 is a top view, partially in section, illustrating still another alternative embodiment of the present invention, showing still another variation of the fastening means shown in FIGS. 1–3, wherein the fastening means comprise a pair of elastic members which have been twisted together at one end so as to form a single twisted central portion which extends into the distal portion of the body;

FIG. 29 is a side elevational view of the anchor shown in FIG. 28;

FIG. 30 is a rear end view of the anchor shown in FIG. 28;

FIG. 31 is a top view, partially in section, of yet another alternative embodiment of the present invention, showing still another variation of the fastening means, wherein the fastening means comprise multiple parts;

FIG. 32 is a side elevational view of the anchor shown in FIG. 31;

FIG. 33 is a rear end view of the anchor shown in FIG. 31;

FIG. 34 is a top view, in section, of the crimpable ferrule shown in FIG. 31, illustrating a pair of longitudinally-extending cylindrical openings;

FIG. 35 is a rear end view of the crimpable ferrule of FIGS. 31 and 34, illustrating the two cylindrical openings;

FIG. 36 is a top view, partially in section, illustrating yet another alternate embodiment of the present invention, showing another variation of the fastening means shown in FIGS. 1–3, wherein the fastening means comprise a looped central portion extending into the distal portion of the anchor body;

FIG. 37 is a side elevational view of the anchor shown in FIG. 36;

FIG. 38 is a rear end view of the anchor shown in FIG. 36;

FIG. 39 is a top view, partially in section, illustrating still another embodiment of the present invention, showing yet another variation of the fastening means shown in FIGS. 1–3, wherein the fastening means comprise a compound spring;

FIG. 40 is a side elevational view of the anchor shown in FIG. 39;

FIG. 41 is a rear end view of the anchor shown in FIG. 49;

FIG. 42 is a top view, partially in section, showing a further novel embodiment of the present invention, in which a pair of fastening means are enclosed within the body;

FIG. 43 is a side elevational view of the anchor shown in FIG. 42;

FIG. 44 is a rear end view of the anchor shown in FIG. 43;

FIG. 45 is a top view, partially in section, illustrating still another embodiment of the present invention, wherein the fastening means extend perpendicularly to the body's longitudinal axis;

FIG. 46 is a side elevational view of the anchor shown in FIG. 45;

FIG. 47 is a rear end view of the anchor shown in FIG. 45;

FIG. 48 is an exploded side elevational view of a typical installation tool of the sort which may be used to insert the anchor of the present invention into a bone hole;

FIG. 49 is an enlarged side elevational view, in section, showing the tubular sleeve member of the installation tool of FIG. 48;

FIG. 50 is a plan view of the same tubular sleeve member, as taken along line 50—50 of FIG. 49;

FIG. 51 is a side elevational view showing an anchor formed in accordance with the present invention, and the installation tool of FIG. 48, with the two devices being assembled together in preparation for inserting the anchor into the hole in the target bone;

FIG. 52 is a partial side elevational view of the assembly of FIG. 51 positioned adjacent the target bone;

FIG. 53 is a partial side elevational view of the assembly of FIG. 51 inserting the anchor into the target bone;

FIG. 54 is a partial side elevational view showing an alternative form of elongated shaft which may be used in forming an installation tool of the sort shown in FIG. 48; and FIG. 55 is an enlarged partial side elevational view showing selected details of the elongated shaft shown in FIG. 54.

DETAILED DESCRIPTION OF THE PREFERRED EMBODIMENTS

Looking first at FIGS. 1, 2, and 3, there is shown an anchor 3 which comprises a preferred embodiment of the present invention. Anchor 3 generally comprises a body 6, attachment means 9 and fastening means 12.

Body 6 has a longitudinal axis 15 and comprises a distal portion 18 having a conical end surface 21, a proximal portion 24 having an end surface 27, and a middle portion 30 extending between distal portion 18 and proximal portion 24. Conical end surface 21 eases insertion of the anchor into a hole formed in a workpiece. Body 6 has a maximum cross-section (as taken transverse to its longitudinal axis 15) which is only slightly smaller than the diameter of the target bone hole, as will hereinafter be disclosed in further detail.

At least two longitudinally-extending channels 33 extend along the outer surface of body 6. Each longitudinal channel 33 opens on end surface 27 and has a substantially constant depth throughout its length.

In the preferred embodiment, body 6 may comprise a polymer, such as polysulfone, PEEK, Nylon or Delrin.

Alternatively, body 6 may be formed out of any one of the many bioabsorbable materials well known in the art. For example, anchor body 6 might be formed out of materials such as homo and copolymers of glycolide and trimethylene carbonate, homo and copolymers of lactide and glycolide, homo and copolymers of polylactic acid, or a blend of these homopolymers and copolymers. Anchor body 6 might also be coated with longer lasting materials, e.g. caprolactone and glycolide homo and copolymers, or glycolide and lactide homo and copolymers. Of course, the exact composition of such absorbable anchor bodies will vary according to the absorption and rigidity characteristics desired. Such compositions are well known to persons skilled in the art.

In the following detailed description, body 6 and its various alternative embodiments will be disclosed assuming fabrication from a material of the sort described above. It will be understood, however, that these same embodiments may be fabricated from another non-absorbable polymer, or from a non-absorbable material which is not a polymer, or from another absorbable material. Alternatively, these same embodiments may be fabricated from metal, using conventional metal-forming techniques, without departing from the scope of the present invention.

Attachment means 9 extend through body 6 and provide a means for attaching the desired object to body 6. Attachment means 9 preferably comprise a bore 36 extending transversely through body 6 and communicating with longitudinal channels 33. Advantageously, when the anchor of the present invention comprises a suture anchor and that anchor is installed in a bone hole, the suture can be attached to body 6 using attachment means 9 so that it is able to slide freely relative to the anchor. More particularly, a suture that passes through attachment means 9 can pass by proximal portion 24 of body 6 via longitudinally-extending channels 33. In essence, longitudinally-extending channels 33 provide a clearance between the inner surface of the bone hole and the suture so that the suture will not be abraded during anchor insertion and, consequently, will not bind against the bone hole inner surface after anchor insertion. Attachment means 9 may be provided at either the distal, proximal, or middle portions of anchor body 6. In the preferred embodiment shown in FIGS. 1–3, attachment means 9 comprise the bore 36 extending transversely through the anchor body's proximal portion 4. The portion of bore 36 located closest to proximal end surface 27 forms a smoothly contoured bearing surface 39 (FIG. 2). Smoothly contoured bearing surface 39 is formed so that it is free of sharp edges. Accordingly, a length of suture threaded through bore 36 and engaging surface 39 may be slid along that bearing surface, if desired, after the anchor has been deployed in the bone hole. It will be appreciated that by forming attachment means 9 as a transverse bore 36 located at the proximal end of the anchor, any forces applied to the free ends of the suture after the anchor has been set in bone will not tend to induce rotational torque on the anchor.

In the preferred embodiment shown in FIGS. 1–3, fastening means 12 comprise a curved central portion 42 and a pair of bone-engaging means 45. Curved central portion 42 is fixedly positioned within body 6 adjacent to the point where middle portion 30 meets distal portion 18. Curved central portion 42 preferably comprises a substantially rectangular cross-section and is curved so that it extends proximally outward with respect to body 6. The pair of bone-engaging means 45 comprise elongate beams which extend proximally outwardly from curved central portion 42 by a predetermined distance from body 6. Each of the bone-engaging means 45 further comprise an outwardly curving end portion 48, when in their normal, unstressed condition. End portions 48 are curved outwardly to further enhance engagement of the anchor with the adjacent bone surface when the anchor is disposed in the target bone hole. Bone-engaging means 45 are cantilevered and preferably have a substantially rectangular cross-section. It will be understood, however, that other cross-sections (including circular, square, ellipsoidal, and polygonal) may also be used.

It is further to be appreciated that the lengths (and widths) of bone-engaging means 45 and longitudinally-extending channels 33 are carefully sized relative to one another in order that the bone-engaging means 45 may be fully received in longitudinally-extending channels 33, without contacting a suture positioned in attachment means 9, when bone-engaging means 45 are deformed during anchor deployment.

Typically, bone-engaging means 45 are disposed about longitudinal axis 15 and cantilevered to curved central portion 42. Bone-engaging means 45 and curved central portion 42 are arranged in this manner so that during anchor insertion into a bone hole or bone tunnel, the stress generated by the deformation of fastening means 12 is, in large part, supported only by curved central portion 42. Thus, novel fastening means 12 substantially reduce the level of stress applied to body 6 during insertion of the anchor in a bone hole or bone tunnel.

In the preferred embodiments shown in FIGS. 1–3, curved central portion 42 is formed integral with and of the same material as bone-engaging means 45. However, curved central portion 42 may also be a separate structure made of a different material, as will hereinafter be disclosed in further detail. In any case, central portion 42 of fastening means 12 must be made of a suitable material such that it is capable of withstanding the stresses applied to it as a result of the deformation of cantilevered bone-engaging means 45.

Preferably, bone-engaging means 45 are formed out of a pseudoelastic shape memory alloy of the type disclosed in U.S. Pat. No. 4,665,906 entitled "Medical Devices Incorporating SIM Alloy Elements", issued May 19, 1987 to Jervis, which patent is specifically incorporated herein by reference. By way of example, one such pseudoelastic shape memory alloy might be a nickel titanium alloy such as Nitinol, which is available from Flexmedics of Minneapolis, Minn. among others. The use of such a material, in combination with the normal orientation of bone-engaging means 45 relative to anchor body 6, permits bone-engaging means 45 to initially deflect inwardly to the extent required to permit the anchor to move forward in a bone hole or bone tunnel, yet still resiliently "spring back" toward their normal, outwardly projecting position so as to prevent the anchor from withdrawing back out of the bone hole or bone tunnel.

The anchor of the present invention may vary in both the size and shape of its constituent body portions and/or its fastening means.

One such alternative embodiment of the anchor body is shown in FIGS. 4–6. More particularly, there is shown an anchor 51 which comprises an anchor body 54 and fastening means 12. Fastening means 12 are substantially identical to the fastening means 12 described above in connection with the anchor 3 shown in FIGS. 1–3. Body 54 has a distal portion 18 similar to that disclosed and illustrated in the anchor 3 shown in FIGS. 1–3. Body 54, however, further comprises middle and proximal portions that include at least two flattened side surfaces 57. More particularly, proximal portion 24 and middle portion 30 comprise flattened surfaces 57 that are recessed relative to distal portion 18. The depth of flattened surfaces 57 relative to distal portion 18 is at least substantially equal to the thickness of bone-engaging means 45. Flattened surfaces 57 extend proximally from the point where distal portion 18 meets middle portion 24.

Attachment means 9 extend diametrically through body 54 such that when the anchor comprises a suture anchor and the anchor is deployed, the attached suture will be free to slide relative to the anchor as disclosed previously in connection with the anchor 3 shown in FIGS. 1–3. Thus, flattened surfaces 57 function in a manner similar to the aforementioned longitudinally-extending channels 33, in the sense that they provide clearance for bone-engaging means 45 and a length of suture between the inner surface of a bone hole or bone tunnel and the middle and proximal portions of body 54.

Figure 9:
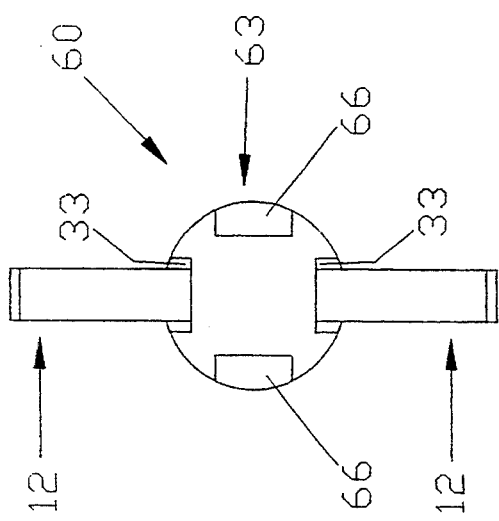
FIG. 9 is a rear end view of the anchor shown in FIG. 7.
Figure 7:
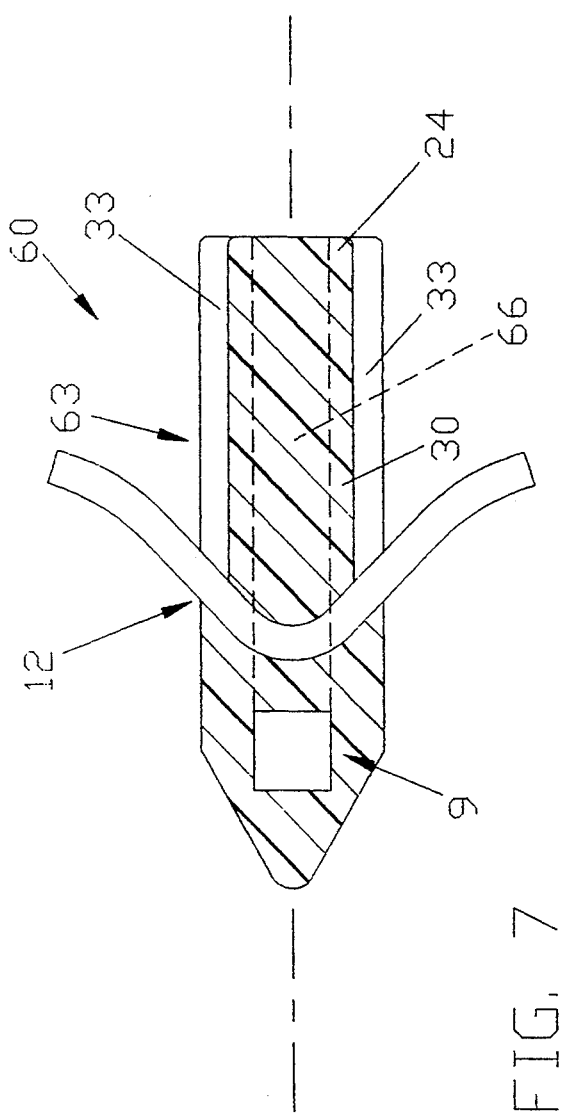
FIG. 7 is a top view, partially in section, of another alternative embodiment of the present invention, showing another variation of the anchor body shown in FIGS. 1-3, wherein the attachment means are located in the distal portion.
Figure 8:
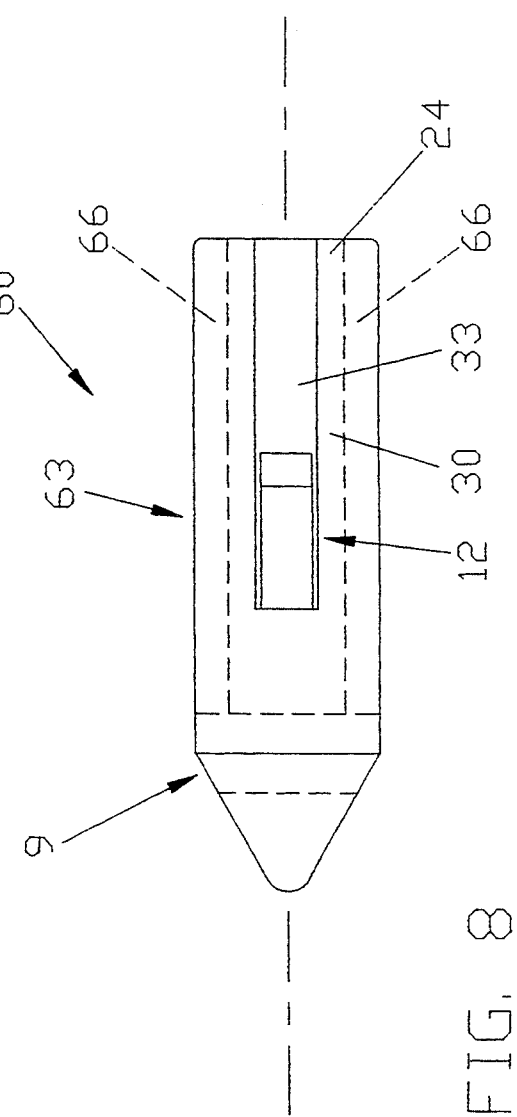
FIG. 8 is a side elevational view of the anchor shown in FIG. 7.

Looking next at FIGS. 7–9, there is shown an anchor 60 which comprises a body 63, attachment means 9 and fastening means 12. Fastening means 12 are substantially identical to the fastening means 12 described above in connection with the anchor 3 shown in FIGS. 1–3. Body 63 is substantially identical to the body 6 described above in connection with the anchor 3 shown in FIGS. 1–3, except that attachment means 9 are positioned in the distal portion of body 63 rather than in the middle or proximal portions thereof, and attachment means 9 extend through body 63 perpendicular to the length of fastening means 12. Accordingly, longitudinally-extending channels 66 extend proximally from distally-positioned attachment means 9 and through middle portion 30 and proximal portion 24 to provide a path for suture or the like extending through attachment means 9. Of course, it will also be appreciated that longitudinally-extending channels 66 may extend from any portion of the anchor body having attachment means 9 located therein.

What has been described above are preferred embodiments of a novel anchoring device having a body comprising polymeric or bioabsorbable materials and fastening means comprising a plurality of bone-engaging means made out of a pseudoelastic shape memory alloy. It is to be appreciated, of course, that various modifications may be made to the fastening means without departing from the scope of the present invention.

A critical aspect of the novel bone anchor of the present invention is the positioning of the central portion of the fastening means within the anchor body so as to prevent rotation of the fastening means with respect to the anchor body. If the fastening means are allowed to rotate within the anchor body, damaging stresses will be generated and transferred to the anchor body. Additionally, the anchor body may rotate within the bone hole during insertion. Both of these undesirable effects can be further guarded against by adding various body engaging means to the central portion of the fastening means.

For instance, and now looking at FIGS. 10–12, there is shown an anchor 69 which comprises a body 6, attachment means 9 and fastening means 72. Body 6 and attachment means 9 are substantially identical to the body 6 and attachment means 9 described above in connection with the anchor 3 shown in FIGS. 1–3. Fastening means 72 are substantially identical to fastening means 12 described above in connection with the anchor 3 shown in FIGS. 1–3, except for comprising a notched central portion 75. Notched central portion 75 comprises cutout portions 78 positioned on one or more sides thereof. Cutout portions 78 help to improve mechanical engagement between central portion 72 and body 6, thus reducing the likelihood of fastening means 72 rotating relative to body 6. While rectangular cutout portions are illustrated in FIG. 10, it will also be appreciated that other cross-sections (including crescent, round, triangular, etc.) are also within the scope of the present invention. Furthermore, notched central portion 75 may be used in combination with body 54 of FIGS. 4–6, or in combination with body 63 of FIGS. 7–9.

Another example of body engaging means is seen in FIGS. 13–15. More particularly, there is shown an anchor 81 which comprises a body 6, attachment means 9 and fastening means 84. Body 6 and attachment means 9 are substantially identical to the body 6 and attachment means 9 described above in connection with the anchor 3 shown in FIGS. 1–3. Fastening means 84 have a flattened central portion 87. Flattened central portion 87 has a rectangular cross-section, is preferably round, and includes a centrally positioned through-hole 90. It will be appreciated, of course, that various other shapes and cross-sections are also within the scope of the present invention.

Flattened central portion 87 is positioned such that bone-engaging means 45 may extend proximally outward in the same manner as disclosed previously in connection with the discussion of fastening means 12. Flattened central portion 87 and through-hole 90 increase the mechanical interaction between central portion 87 and the material comprising body 6. Central portion 87 further includes indented portions 93 circumferentially positioned on the edges of central portion 87 so as to further fixedly engage the material of body 6. Again, alternative body 54 of FIGS. 4–6, the alternative positioning of the attachment means 9 of FIGS. 7–9, and/or the alternative bone-engaging means of the sort that are disclosed hereinafter would be equally appropriate in combination with fastening means 84.

It will also be appreciated that other modifications to the central portion of the fastening means are possible so as to prevent rotation of the fastening means and to minimize any stresses transferred to the anchor body during bone engagement. By way of example, and turning now to FIGS. 16–18, there is shown an anchor 96 comprising a body 6, attachment means 9 and fastening means 99. Body 6 and attachment means 9 are substantially identical to the body 6 and attachment means 9 described above in connection with the anchor 3 shown in FIGS. 1–3. Fastening means 99 comprise a central portion 102 and bone-engaging means 45, arranged in the same manner as disclosed previously in connection with the discussion of fastening means 12, except that central portion 102 is formed with a smaller radiused curve so as to project slightly further into distal portion 18. Thus, central portion 102 helps to impede rotation of fastening means 99 by mechanically engaging distal portion 18 of body 6.

Bone-engaging means 45 extend radially outwardly from each side of central portion 102, and normally project axially rearward relative to the anchor's distal portion 18. Bone-engaging means 45 may or may not have an outwardly curving end portion 48 as disclosed previously in connection with bone-engaging means 45 as shown in FIGS. 1-3. It will be understood that notched central portion 75 of FIGS. 10-12, the alternative body 54 of FIGS. 4-6, and/or the alternative location of attachment means 9 as shown in FIGS. 7-9 may all be used in conjunction with fastening means 99.

The central portion of the fastening means may be extended even further into distal portion 18 as an obstacle to rotation of the fastening means.

More specifically, and looking now at FIGS. 19-21, there is shown an anchor 105 comprising a body 6, attachment means 9, and fastening means 108. Body 6 and attachment means 9 are substantially identical to the body 6 and attachment means 9 described above in connection with the anchor 3 shown in FIGS. 1-3. Fastening means 108 have a linearly-projecting central portion 111 formed such that it projects from the anchor body's distal portion 18 proximally outward toward the distal ends 114 of bone-engaging means 45. It is also to be appreciated that while fastening means 108 are shown in conjunction with body 6 in Figs. 19-21, fastening means 108 could also be combined with the alternative body 54 of FIGS. 4-6 or the alternative body 63 of FIGS. 7-9, etc.

Linearly-projecting central portion 111 comprises a generally "V"-shaped projection formed in a similar manner to the central portion 102 disclosed previously in connection with the anchor 96 shown in FIGS. 16-18, except that it has a very small radiused curve at its apex 117. Apex 117 is positioned within body 6 so that the linearly-projecting central portion 111 extends proximally therefrom so as to meet the distal ends 114 of bone-engaging means 45. By projecting from distal portion 18 of body 6, linearly-projecting central portion 111 provides rotational stability to fastening means 108 during insertion of the anchor into a bone hole or bone tunnel. Bone-engaging means 45 may comprise any of the designs previously disclosed, e.g. that shown in FIGS. 1-3 or FIGS. 16-18.

Furthermore, as seen in FIGS. 21A-21C, linearly-projecting central portion 111 may be twisted about the anchor's longitudinal axis so as to form a twisted linearly-projecting central portion 111A in an anchor 105A. Twisted linearly-projecting central portion 111A helps provide additional mechanical engagement between fastening means 108A and body 6.

A further alternative embodiment for the central portion of the fastening means is shown in FIGS. 22-24. More particularly, there is shown an anchor 120 comprising a body 6, attachment means 9 and fastening means 123. Body 6 and attachment means 9 are substantially identical to the body 6 and attachment means 9 described above in connection with the anchor 3 shown in FIGS. 1-3. Fastening means 123 comprise a split beam construction. Again, while fastening means 123 are shown in conjunction with body 6 in FIGS. 22-24, fastening means 123 could also be combined with the alternative body 54 of FIGS. 4-6, the alternative body 63 of FIGS. 7-9, etc.

Split beam fastening means 123 comprise a bar of pseudoelastic material that has been split longitudinally along a portion of its length, and then spread apart to form a pair of cantilevered bone-engaging means 45, substantially identical to those previously discussed. The linearly-projecting rectangular central portion 126 of fastening means 123, formed by the unsplit end of the bar, projects into distal portion 18 of body 6 from the distal ends 114 of bone-engaging means 45. Linearly-projecting rectangular central portion 126 extends into distal portion 18 so as to provide added rotational stability to fastening means 45.

Although a rectangular split beam construction is shown in FIGS. 22-24, other cross-sections such as circular or elliptical also may be employed. Thus, for example, and looking now at FIGS. 25-27, an anchor 129 is shown. Anchor 129 comprises a body 6, attachment means 9 and fastening means 132. Body 6 and attachment means 9 are substantially identical to the body 6 and attachments means 9 described above in connection with the anchor 3 shown in FIGS. 1-3. Fastening means 132 are formed by splitting a tube of generally pseudoelastic metal alloy longitudinally along a portion of its length and diametrically across its width. It is to be appreciated that while fastening means 132 is shown in conjunction with body 6 in Figs. 25-27, fastening means 132 could also be combined with the alternative body 54 of FIGS. 4-6 or the alternative body 63 of FIGS. 7-9, etc.

Fastening means 132 comprise a linearly-projecting tubular central portion 135 and a pair of bone-engaging means 138. Linearly-projecting tubular central portion 135 extends into the body's distal portion 18. Advantageously, tubular central portion 135 may be filled with the material comprising body 6 during fabrication of the anchor. Thus filled with polymeric or bioabsorbable material, tubular central portion 135 further acts as a stabilizer, preventing unwanted rotation of fastening means 132. Bone-engaging means 138 of fastening means 132 comprise arcuate cross-sections, as seen in FIGS. 26 and 27.

It is also to be appreciated that the fastening means of the present invention can be formed out of separate constituent parts connected together during assembly.

Thus, for example, in FIGS. 28-30 an anchor 141 is shown which comprises a body 6, attachment means 9, and fastening means 144. Body 6 and attachment means 9 are substantially identical to the body 6 and attachment means 9 described above in connection with the anchor 3 shown in FIGS. 1-3. Fastening means 144 comprise two separate elongate elastic members 147 and 150 which have been joined together at one end so as to form a composite linearly-projecting central portion 153 (FIG. 28). Linearly-projecting central portion 153 is similar in all other respects to central portion 126 shown in FIG. 22. Elastic members 147 and 150 extend proximally outward from linearly-projecting central portion 153 so as to form bone-engaging means 45. Elastic members 147 and 150 are twisted together along a portion of their length so as to form the composite central portion 153. In all other respects, fastening means 144 is comparable in performance to split bar fastening means 123 shown in FIGS. 22-24. It is also to be appreciated that while fastening means 144 are shown in conjunction with body 6 in FIGS. 28-30, fastening means 144 could also be combined with body 54 of FIGS. 4-6 or body 63 of FIGS. 7-9, etc.

In another example of multi-part fastening means, an anchor 156 is shown in FIGS. 31-35. Anchor 156 comprises a body 6, attachment means 159 and fastening means 162. Body 6 is substantially identical to the body 6 described above in connection with the anchor 3 shown in FIGS. 1-3. Attachment means 159 preferably comprise a bore 163 extending transversely through body 6. A pair of longitudinally-extending channels 165 extend proximally therefrom, to provide a passageway for receiving a suture passing through bore 163 and permitting it to move relative to body 6 after deployment of the anchor in bone, in the manner previously discussed above. Fastening means 162 comprise a central portion 168 and a pair of curved barbs 171. Central portion 168 in turn comprises a separate pair of crimpable ferrules 174 adapted to receive the distal ends of curved barbs 171. Curved barbs 171 are positioned in each ferrule 174 such that curved barbs 171 curve outwardly relative to the center line of each ferrule 174 (FIGS. 1 and 34). Each barb 171 is curved in its unstressed state.

Central portion 168, with outwardly curved barbs 171 inserted therein, is crimped so that curved barbs 171 are clamped in central portion 168. Thus, multi-part fastening means 162 is formed having the desired bone-engaging means extending outwardly from central portion 168. Central portion 168 is positioned within body 6.

It will be appreciated that 3, 4 or even more cantilevered barbs 171 may be attached to a suitably adapted central portion 168 to provide the desired number of bone-engaging means. Similarly, crimpable ferrules 174 of central portion 168 may be disposed at an angle relative to the longitudinal axis of central portion 168, so that straight barbs may be crimped to central portion 168 and still extend outwardly therefrom in the manner disclosed in FIGS. 13–15, 16–18, 19–21, 22–24, and/or 28–30. Furthermore, it is also to be appreciated that while fastening means 162 are shown in conjunction with a body 6 in FIGS. 31–35, fastening means 162 could also be combined with body 54 of FIGS. 4–6 or body 63 of FIGS. 7–9, etc.

It will also be appreciated that the novel fastening means of the present invention may comprise more complex shapes. More particularly, and turning now to FIGS. 36–38, an anchor 177 is shown which comprises a body 6, attachment means 180 and fastening means 183. Body 6 is substantially identical to the body 6 described above in connection with the anchor 3 shown in FIGS. 1–3. Attachment means 180 preferably comprise a bore 186 extending transversely through body 6. A pair of longitudinally-extending channels 189 extend proximally therefrom, to provide a passageway for receiving a suture passing through bore 186 and permitting it to move relative to body 6 after deployment of the anchor in bone, in the manner previously described above.

Fastening means 183 form a single turn coil spring. Single turn coil spring 183 comprises a central portion 192 and a pair of bone-engaging means 45 formed integral therewith. Single turn central portion 192 is positioned such that it projects into distal portion 18 of body 6. Single turn central portion 192 is disposed around bore 186 of attachment means 180. It is also to be appreciated that while fastening means 183 are shown in conjunction with a body 6 in FIGS. 36–38, fastening means 183 could also be combined with body 54 of FIGS. 4–6 or body 63 of FIGS. 7–9, etc.

Still another anchor 195 is disclosed in Figs. 39–41. Anchor 195 comprises a body 198, attachment means 201 and fastening means 204. As seen in FIG. 39, body 198 comprises a distal portion 207 similar to distal portion 18 shown in FIG. 1, a proximal portion 210 similar to proximal portion 24 shown in FIG. 1, and a middle portion 213. Middle portion 213 further comprises an open cavity 216 in which compound spring fastening means 204 are positioned and allowed to float freely. Body 198 may be manufactured by fabricating distal portion 207 separately from middle and proximal portions 213 and 210. To assemble anchor 195, compound spring fastening means 204 is first inserted into middle portion 213, and then distal portion 207 is attached to middle portion 213 by various means such as bonding or ultrasonic welding. For example, with the anchor 195 shown in FIG. 39, distal portion 207 has been attached to middle portion 213 along the parting line 217.

Compound spring fastening means 204 comprise two longitudinally-extending elastic beams 219 that extend from central portion 222. Central portion 222 is located adjacent attachment means 201 in proximal portion 210 (FIG. 39). Each elastic beam 219 fixedly engages bone-engaging means 225 at intermediate portions 228. Bone-engaging means 225 extend outwardly from intermediate portions 228 in the same manner as disclosed previously in connection with the discussion of fastening means 12 or 84.

In operation, bone-engaging means 225 engage the outer edge of a bone hole (not shown) along a portion of their length. As this occurs, longitudinally-extending elastic beams 219 deflect inwardly, thus allowing bone-engaging means 225 to move inwardly in response to interaction with the bone hole. When longitudinally-extending elastic beams 219 deflect, however, bone engaging means 225 do not deflect relative to intermediate portions 228. Once longitudinally-extending elastic beams 219 deflect to the point where intermediate portions 228 engage each other within open cavity 216, bone-engaging means 225 begin to deflect with respect to intermediate portions 228 in response to interaction of the anchor with the bone hole. Compound spring fastening means 204 deflect in such a manner as to maintain a fully elastic deformation of the material. Central portion 222 loops around attachment means 201, thus providing added support for a suture passing therethrough.

It is also possible to place two identical fastening means in body 6 of FIGS. 1–3, body 54 of FIGS. 4–6 or body 63 of FIGS. 7–9 so as to increase the anchor's engagement with the target bone. As seen in FIGS. 42–44, an anchor 231 is shown which comprises a body 6, attachment means 9 and fastening means 12A and 12B. Body 6 and attachment means 9 are substantially identical to the body 6 and attachment means 9 described above in connection with the anchor 3 shown in FIGS. 1–3. Fastening means 12A and 12B are each substantially identical to the fastening means shown in FIGS. 1–3. Fastening means 12A and 12B are placed along the longitudinal axis 15 of body 6, their central portions being rotated 90° with respect to one another. Bone-engaging means 45A and 45B of elastic members 12A and 12B extend in equally circumferentially-spaced relationship to one another. It will be appreciated that notched central portion 78 of FIGS. 10–12 may also be incorporated in fastening means 12A or 12B, as well as the various bone-engaging means embodiments heretofore disclosed in FIGS. 13–15, 16–18, 19–21, 22–24, 25–27, 28–30 and 36–38.

FIGS. 45–47 disclose a non-preferred, but nonetheless fully operative, embodiment of the present invention. Anchor 234 comprises a body 237 having a distal portion 240, a proximal portion 243, and a middle portion 246 extending therebetween. Attachment means 249 are positioned in body 237 so as to function as previously disclosed above in connection with attachment means 9. Straight fastening means 252 are fixedly positioned within body 237. Straight fastening means 252 include a central portion 255 extending diametrically through body 237 and include bone-engaging means 258 extending from both sides thereof.

The various novel anchoring devices disclosed above may be inserted into a bone hole using various insertion tools of the sort well known in the art. By way of example, an insertion tool such as that disclosed in the above-identified U.S. Pat. No. 5,217,486 can be utilized to deploy an anchor formed in accordance with the present invention. For example, the installation tool shown in FIGS. 48–55 may be used to apply the anchoring devices of the present invention.

More specifically, an installation tool 402 is disclosed which includes an elongated shaft 404 and a tubular sleeve 406. Shaft 404 is preferably formed from metal such as stainless steel, and sleeve 406 is preferably formed from a polymeric, bio-compatible plastic material.

Shaft 404 comprises a distal end portion 408 having a first relatively small diameter, an intermediate portion 410 having a second relatively intermediate diameter, and a proximal end portion 412 having a third relatively large diameter. A first shoulder 414 is formed where distal portion 408 meets intermediate portion 410, and a second shoulder 416 is formed where intermediate portion 410 meets proximal portion 412. Shaft 404 terminates in a distal end surface 417. A handle 418 is attached to shaft 404 adjacent to its proximal end 412. Handle 418 may be generally rectangular in shape and includes suture-receiving slots 420 adapted to hold, through frictional engagement, a suture extending from a suture anchor mounted to tool 402.

A circumferential groove 422 is formed in the outer surface of intermediate portion 410 approximately midway along its length. In the drawings, groove 422 extends all the way around the circumference of intermediate portion 410, however, groove 422 may also be formed as a series of separate, circumferentially-extending groove arcs separated by lands, or as a series of discrete, circumferentially-spaced indentations, if desired.

Tubular sleeve 406 has a distal end 424, a proximal end 426, and an outer diameter substantially equal to the diameter of the shaft's proximal portion 412. A central bore 428 passes through sleeve 406. A counterbore 430 is formed at the distal end of sleeve 406. Counterbore 430 intersects bore 428 at a shoulder 432. A rib 434 extends radially into bore 428 adjacent the proximal end of the sleeve. Rib 434 defines a diametrical opening 436 which is smaller than the internal diameter of bore 428. In the event that shaft groove 422 is broken up into discrete arcs or indentations, rib 434 is correspondingly broken.

A plurality of circumferentially-spaced, longitudinally-extending slots 438, 440, 442, and 444 extend through the side wall of sleeve 406, opening on distal end 424 and extending proximally therefrom. The purpose of these slots is to accommodate the suture anchor's bone-engaging means and suture, both of which extend outwardly from the anchor body when the anchor is mounted partially within tubular sleeve 406, as will hereinafter be described in further detail. Accordingly, in the embodiment shown, the anchor's bone-engaging means can be received by slots 440 and 444 and/or slots 438 and 442, depending on the particular construction of the bone anchor, and the portions of suture extending outwardly from the anchor's attachment means can be received by slots 440 and 444 and/or slots 438 and 442, depending on the particular construction of the bone anchor. The anchor's bone-engaging means, and slots 438 and 442 are provided to receive the portions of suture extending outwardly from the anchor's attachment means. It will, of course, also be understood that the number and arrangement of the slots 438, 440, 442 and 444 may be varied according to the specific configuration of the anchor, i.e., if there are a plurality of bone-engaging means on the anchor, more slots can be provided to accommodate them, and if the object attached to the anchor's attachment means requires it, the size and number of the slots can be adjusted to accommodate the portions of the object attached to the attachment means. In the following example, the exemplary bone anchor will comprise two bone-engaging means which will be received in slots 440 and 444, and two lengths of suture which will be received in slots 438 and 442.

Tubular sleeve 406 is sized so that its central bore 428 has an inside diameter just slightly larger than the outside diameter of the shaft's intermediate portion 410, but smaller than the outside diameter of the suture anchor's body; its counterbore 430 has an inside diameter just slightly larger than the outside diameter of the suture anchor's body; and its rib 434 has a diametrical opening 436 slightly less than the outside diameter of the shaft's intermediate portion 410 but slightly larger than the circle enscribing the floor of shaft groove 422.

In view of this construction, sleeve 406 may be telescoped onto the shaft's intermediate portion 410 so that the sleeve's rib 434 makes a tight sliding fit with the outside diameter of the shaft's intermediate portion 410, with the sleeve being movable between first and second operative positions. In the first of these positions, i.e., that shown in FIGS. 51 and 52, rib 434 resides in the shaft's groove 422 so as to yieldably lock sleeve 406 to shaft 404. In the second of these positions, i.e., that shown in FIG. 53, the proximal end 426 of the sleeve 406 engages the shoulder 416 formed at the intersection of intermediate portion 410 and proximal portion 412. Shaft 404 and sleeve 406 are sized so that when sleeve 406 is disposed in its first position so that its rib 434 resides in shaft groove 422, the distal end surface 417 of shaft 404 will terminate short of sleeve shoulder 432 (FIG. 51), but when sleeve 406 is disposed in its second position so that its proximal end 426 engages shaft shoulder 416, distal end surface 417 of shaft 404 will project outward from the distal end of sleeve 406 (FIG. 53).

It is also to be appreciated that shaft 404 and tubular sleeve 406 are sized relative to one another so that sleeve 406 can rotate circumferentially about shaft 404 when sleeve 406 is in either of its first and second operative positions, or at any position therebetween.

It is to be appreciated that when sleeve 406 is in the position shown in FIGS. 51 and 52, i.e., so that sleeve rib 434 is disposed in shaft groove 422, an anchor may be disposed in sleeve 406 so that the proximal end surface of the anchor engages and is stopped by sleeve shoulder 432 and so that the distal end of the anchor body projects out of the distal end of sleeve 406. Sleeve slots 438, 440, 442, and 444 are sized sufficiently long so that when an anchor body is disposed in sleeve 406 and has its proximal end engages sleeve shoulder 432, the anchors' bone-engaging means and suture need not engage the proximal ends of slots 438, 440, 442, and 444.

Installation tool 402 is used as follows.

First, the tool has its sleeve 406 placed in its aforementioned first position, i.e., so that it is in the position shown in FIG. 51 wherein the sleeve's rib 434 is positioned in the shaft's groove 422. Then a suture anchor 502 having bone-engaging means 504 and a suture 506 is loaded into the distal end of tubular sleeve 406 so that the distal end of the anchor engages sleeve shoulder 432, and so that bone-engaging means 504 reside in two diametrically opposed sleeve slots (e.g. sleeve slots 440, 444) and the suture lengths 506 emanating from the anchor reside in the remaining two diametrically-opposed sleeve slots (e.g. sleeve slots 438, 442), with bone-engaging means 504 and the suture lengths 506 not necessarily engaging the proximal ends of slots 438, 440, 442, and 444. It will be appreciated that when the system components are in the foregoing positions, the shaft's distal end surface 417 will terminate short of the anchor's proximal end surface, and the distal portion of the anchor body will extend out the distal end of tool 402. See FIG. 51. Preferably the free ends of the suture are wrapped into handle slots 420 under slight tension so as to keep the suture ends under control and so as to help hold the anchor body to the distal end of tubular member 406.

Next, tool 402 is manipulated so as to bring the distal portion of the anchor body into the top of the hole 602 formed in workpiece 604. As noted above, the cross-section of the anchor's body will be only slightly smaller than the diameter of hole 602. Accordingly, in this position the distal end 424 of tubular sleeve 406 will bear against the workpiece's top surface 606 which surrounds the anchor-receiving hole 602. See FIG. 52.

From this position the anchor body may be driven into hole 602 so as to achieve its desired anchoring location within the bone. This is accomplished by driving shaft handle 418 downward, until shaft groove 422 moves past sleeve rib 434. Shaft 404 continues moving downward until shoulder 416 of shaft 404 engages the sleeve's proximal end 426. This action causes the distal end surface 417 of shaft 404 to engage the proximal end of the anchor body and drive it downward into bone hole 602. See FIG. 53. As this deployment action occurs, the anchor's bone-engaging means 504 engage the portions of bone 604 which define hole 602 and, due to this engagement, are forced inwardly to the extent required to permit the suture anchor to pass down the bone hole. At the same time, of course, the resilient nature of bone-engaging means 504 causes them to springly engage the surrounding bone and thereby cause the suture anchor to be locked to the interior of the bone. Then the proximal ends of suture 506 are released from tool handle 418 and tool 402 is withdrawn from the workpiece, leaving the anchor emplaced in bone 604 and the suture lengths emanating therefrom.

It is to be appreciated that with the installation tool of FIGS. 48–55, only the reduced diameter distal portion 408 of the shaft actually enters the bone hole. The larger diameter intermediate portion 410 and, even more importantly, the anchor engaging and supporting distal end 424 of hollow sleeve 406 remain outside the bone hole at all times. Thus it will be appreciated that bone hole 602 can be sized according to the dimensions of the bone anchor being used, and need not be formed large enough to accommodate the anchor and the engaging and supporting portions of the installation tool as well.

It is also to be appreciated that inasmuch as tubular sleeve 406 is free to rotate circumferentially about shaft 404 when it is in either of its first and second positions, or at any position therebetween, rotational torque imparted to shaft 404 during insertion will not tend to be imparted to the anchor. This is because any rotational torque imparted to handle 418 during insertion will tend to be isolated from the anchor by the rotatable nature of sleeve 406. Thus, any inadvertent rotation of handle 418 during insertion will not tend to cause undesired damage to bone 604 or the anchor's body during insertion.

Looking next at FIGS. 54 and 55, there is shown an alternative form of shaft 404A which may be used in place of the shaft 404 which has been disclosed in connection with the installation tool of FIGS. 48–53. Shaft 404A is identical to shaft 404, except that the groove 422 of shaft 404 has been replaced by generally equivalent rib-engaging means 422A on shaft 404A. More particularly, rib-engaging means 422A comprise a first generally frusto-conical enlargement 460 formed on shaft 410A at the distal side of rib-engaging means 422A, and a second generally frusto-conical enlargement 462 formed on shaft 410A at the proximal side of rib-engaging means 422A. In this shaft embodiment, the diameter of shaft 410A is constant along its length (except for the frusto-conical enlargements 460 and 462) and equal to the diameter of the previous shaft 410. Frusto-conical enlargements 460 and 462 act as a sort of rib-trapping detent along shaft 410A. More particularly, frusto-conical enlargement 460 comprises a sloping distal surface 464 and a radial stopping surface 466, and frusto-conical enlargement 462 comprises a sloping distal surface 467 and a radial stopping surface 468. Radial stopping surfaces 466 and 468 have a larger outside diameter than rib 434 has in inside opening 436. On account of this construction, it will be seen that a sleeve 406 may be loaded onto shaft 404A by moving the sleeve rearward until its rib 434 engages distal sloping surface 464 and slips past it. At this point the sleeve's rib is releasably captured between the radial stopping surface 466 of the distal frusto-conical enlargement 460 and the sloping distal surface 467 of the proximal frusto-conical enlargement 462, so that the sleeve is releasably captured in its aforementioned first position. This is equivalent to the sleeve's rib being releasably captured in the groove 422 of shaft 404. When the sleeve 406 is to thereafter shift to its aforementioned second position, so that rib 434 leaves rib-engaging means 422A and the sleeve's proximal end 426 engages shaft shoulder 416, rib 434 slips past the inclined surface 467.

By forming the proximal frusto-conical enlargement 462 so that its outside diameter at radial stopping surface 468 is only slightly larger than the diameter of shaft 410A, it will be possible for sleeve 406 to pass from its aforementioned first position to its aforementioned second position with relatively little effort, yet sufficient resistance will still be offered to the passage of sleeve 406 along shaft 404A so as to permit a suture anchor to be conveniently loaded into sleeve 406 and carried by the sleeve prior to deployment. In addition, it will be seen that by forming the proximal frusto-conical enlargement 462 so that its outside diameter is only a little larger than the diameter of shaft 410A, the sleeve's rib 434 can also be moved distally down the shaft past radial stopping surface 468 if desired, albeit with somewhat greater effort than is required to pass rib 434 by inclined surface 467. At the same time, it is preferred to form the distal frusto-conical enlargement 460 so that its outside diameter at radial stopping surface 466 is significantly larger than the diameter of shaft 410A, so that it is relatively difficult for rib 434 of sleeve 406 to move distally down the shaft past radial stopping surface 466. While this construction also tends to make it somewhat more difficult to move sleeve rib 434 past enlargement 460 during assembly of the anchor installation tool, in some circumstances this inconvenience may be acceptable so as to ensure that there is little likelihood that sleeve 406 can become disengaged from shaft 404A during use.

Still other variations, modifications, alterations, changes and the like will occur to those skilled in the art in light of the foregoing description of the preferred embodiments of the invention.

Thus, for example, it will be understood that anchor body 6 shown in FIGS. 1–3 may be provided with an additional coupling extending from its proximal end surface 27, where the additional coupling member has a slightly smaller diameter than proximal portion 24. This coupling member can be received in an insertion tool of the type disclosed in U.S. Pat. Nos. 4,968,315 and 5,207,674, both previously disclosed and incorporated herein by reference.

Additionally, while the novel anchor of the present invention has been disclosed in terms of insertion into bone, other assorted workpieces will occur to one skilled in the art.

What is claimed is:

1. An anchor for attaching an object to a bone having a hole formed therein, said anchor comprising:
   a body, attachment means for attaching said object to said body, and fastening means for fastening said anchor within said bone hole;
   said body having a longitudinal axis and a maximum cross-section transverse to said longitudinal axis smaller than the transverse cross-section of said hole in said bone;
   said attachment means comprising an opening in said body; and
   said fastening means comprising a central portion fixedly positioned within said body and further including a plurality of bone-engaging means connected to said central portion of independently of said body and extending outwardly from said central portion such that when said anchor is inserted into said bone hole, said plurality of bone-engaging means engage said bone, with said plurality of bone-engaging means being formed so as to permit said anchor to be inserted into said hole distal end first and adapted to resist withdrawal of said anchor from said hole proximal end first.

2. An anchor according to claim 1 wherein said fastening means comprise a curved central portion and bone-engaging means comprising at least two elongate beams extending outwardly from said curved central portion.

3. An anchor according to claim 2 wherein said at least two elongate beams comprise a distal end and a proximal end, and further wherein said proximal end is curved outwardly relative to said body.

4. An anchor according to claim 2 comprising at least two fastening means.

5. An anchor according to claim 1 wherein said fastening means comprise a pseudoelastic shape memory alloy.

6. An anchor according to claim 1 wherein said body comprises a bioabsorbable material.

7. An anchor according to claim 1 wherein said body comprises a moldable polymer.

8. An anchor according to claim 1 wherein said body comprises a distal portion having a conical distal end surface, a proximal portion having a proximal end surface, and a middle portion extending from said distal portion to said proximal portion, said body further comprising at least two longitudinally-extending channels, said channels extending to said proximal end surface, and further wherein said fastening means comprise a curved central portion and bone-engaging means comprising at least two elongate beams extending outwardly from said curved central portion.

9. An anchor according to claim 8 wherein said at least two elongate beams comprise a distal end and a proximal end, and further wherein said proximal end is curved outwardly relative to said body.

10. An anchor according to claim 9 wherein said central portion linearly projects into said distal portion of said body such that said fastening means resists movement relative to said body.

11. An anchor according to claim 9 comprising at least two fastening means.

12. An anchor according to claim 9 wherein said fastening means comprise body-engaging means for resisting movement of said central portion relative to said body.

13. An anchor according to claim 10 wherein said central portion has been twisted about its longitudinal axis.

14. An anchor according to claim 12 wherein said body-engaging means comprise cut-out portions disposed on said central portion such that said central portion of said fastening means resists movement relative to said body.

15. An anchor according to claim 12 wherein said body-engaging means comprise a flattened central portion having at least one opening extending therethrough.

16. An anchor according to claim 12 wherein said flattened central portion further includes at least one indented portion.

17. An anchor according to claim 12 wherein said fastening means comprise a pseudoelastic shape memory alloy.

18. An anchor according to claim 12 wherein said body comprises a bioabsorbable material.

19. An anchor according to claim 12 wherein said body comprises a moldable polymer.

20. An anchor according to claim 1 wherein said body comprises a distal portion having a conical end surface, a proximal portion having a proximal end surface, and a middle portion extending from said distal portion to said proximal portion, said body further comprising at least two proximally-extending surfaces, said surfaces being recessed relative to said distal portion.

21. An anchor according to claim 20 wherein said fastening means comprise body-engaging means for resisting movement of said central portion relative to said body.

22. An anchor according to claim 20 wherein said central portion linearly projects into said distal portion of said body such that said fastening means resists movement relative to said body.

23. An anchor according to claim 1 wherein said body comprises a distal portion having a conical end surface, a proximal portion having a proximal end surface, and a middle portion extending from said distal portion to said proximal portion, said body further comprising at least two longitudinally-extending channels, said channels extending to said proximal end surface.

24. An anchor according to claim 23 wherein said central portion linearly projects into said distal portion of said body such that said fastening means resists movement relative to said body.

25. An anchor according to claim 24 wherein said fastening means comprise a bar of pseudoelastic shape memory alloy, said bar being split longitudinally along a portion of its length so as to form a pair of elongate beams, with said unsplit portion of said bar comprising said linearly projecting central portion, and said pair of elongate beams being adapted to extend proximally outward of said body.

26. An anchor according to claim 24 wherein said fastening means comprise a tube of pseudoelastic shape memory alloy and having an interior surface, said tube being split longitudinally along a portion of its length so as to form a pair of elongate beams, with said unsplit portion of said tube comprising said linearly projecting central portion and having a portion of said distal portion in engaging contact with said interior surface, and said pair of elongate beams being adapted to extend proximally outward of said body.

27. An anchor according to claim 24 wherein said fastening means comprise at least two elongate beams twisted together along a portion of their length so as to form said central portion, said central portion being positioned within said body so as to linearly project into a distal portion thereof, and wherein said bone-engaging means comprise the unjoined portions of said at least two elongate beams adapted so as to extend outwardly from said central portion and to extend proximally relative to said distal portion of said body.

28. An anchor according to claim 24 wherein said central portion comprises receiving means for fixedly receiving a plurality of bone-engaging means, said plurality of bone-engaging means comprising elongate beams adapted so as to extend outwardly from said central portion and to extend proximally relative to said distal portion of said body, and further wherein said elongate beams are curved outwardly relative to said body.

29. An anchor according to claim 28 wherein said receiving means comprise a crimpable ferrule.

30. An anchor according to claim 24 wherein said fastening means comprise a single turn coil spring comprising a pseudoelastic shape memory alloy, and further wherein said single turn coil spring comprises a central portion of said fastening means that linearly projects into a distal portion of said body and bone-engaging means comprising two elongate beams extending proximally from said central portion and outwardly relative to said body.

31. An anchor according to claim 23 wherein said fastening means comprise compound spring means.

32. An anchor for attaching an object to a bone having a hole formed therein, said anchor comprising:
a body comprising a polymer, attachment means for attaching said object to said body, and pseudoelastic shape memory alloy fastening means for fastening said anchor within said bone hole;
said body having a longitudinal axis and a maximum cross-section transverse to said longitudinal axis smaller than the transverse cross-section of said hole in said bone, and further wherein said body comprises a distal portion having a conical end surface, a proximal portion having an end surface, and a middle portion extending from said distal portion to said proximal portion, said body further comprising at least two longitudinally-extending channels, said channels extending to said proximal end surface;
said attachment means comprising an opening in said body; and
said fastening means comprising a curved central portion fixedly positioned within said body and further including a plurality of bone-engaging means connected to said central portion independently of said body and extending outwardly from said curved central portion;
each of said plurality of bone-engaging means comprising a distal end and a proximal end, and further wherein said distal end is curved outwardly relative to said body such that when said anchor is inserted into said bone hole, said plurality of bone-engaging means engage said bone, with said plurality of bone-engaging means being formed so as to permit said anchor to be inserted into said hole distal end first and adapted to resist withdrawal of said anchor from said hole proximal end first.

33. A system for attaching an object within a bone hole, comprising:
(a) an anchor assembly comprising a body, attachment means for attaching said object to said body, and fastening means for fastening said anchor within said bone hole;
said body having a longitudinal axis and a maximum cross-section transverse to said longitudinal axis smaller than the transverse cross-section of said hole in said bone;
said attachment means comprising an opening in said body; and
said fastening means comprising a central portion fixedly positioned within said body and further including a plurality of bone-engaging means connected to said central portion independently of said body and extending outwardly from said central portion such that when said anchor is inserted into said bone hole, said plurality of bone-engaging means engage said bone, with said plurality of bone-engaging means being formed so as to permit said anchor to be inserted into said hole distal end first and adapted to resist withdrawal of said anchor from said hole proximal end first; and
(b) insertion means for deploying said anchor assembly in a bone hole.

34. A method for attaching an object to a bone comprising:
(a) providing:
(1) means for forming a hole in said bone;
(2) an anchor assembly comprising a body, attachment means for attaching said object to said body, and fastening means for fastening said anchor within said bone hole;
said body having a longitudinal axis and a maximum cross-section transverse to said longitudinal axis smaller than the transverse cross-section of said hole in said bone;
said attachment means comprising an opening in said body; and
said fastening means comprising a central portion fixedly positioned within said body and further including a plurality of bone-engaging means connected to said central portion independently of said body and extending outwardly from said central portion such when said anchor is inserted into said bone hole, said plurality of bone-engaging means engage said bone, with said plurality of bone-engaging means being formed so as to permit said anchor to be inserted into said hole distal end first and adapted to resist withdrawal of said anchor from said hole proximal end first; and (3) insertion means for deploying said anchor assembly in said bone hole;

(b) inserting said anchor into said bone hole distal end first;

(c) actuating said insertion means so as to urge said anchor assembly into said bone hole such that said plurality of bone-engaging means will engage said bone, thus permitting said anchor to enter said bone hole distal end first but to resist withdrawal from said hole proximal end first; and (d) withdrawing said insertion means from said bone hole.

* * * * *